(12) United States Patent
Lee et al.

(10) Patent No.: US 11,129,637 B2
(45) Date of Patent: Sep. 28, 2021

(54) INSTRUMENT FOR SURGERY

(71) Applicant: LIVSMED INC., Seongnam-si (KR)

(72) Inventors: Jung Joo Lee, Seongnam-si (KR); Hee Jin Kim, Seongnam-si (KR); Dong Hwan Bae, Seongnam-si (KR); Dong Kyu Jang, Seongnam-si (KR); Jin Ho Kwon, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 17/059,426

(22) PCT Filed: Dec. 9, 2019

(86) PCT No.: PCT/KR2019/017264
§ 371 (c)(1),
(2) Date: Nov. 27, 2020

(65) Prior Publication Data
US 2021/0244430 A1    Aug. 12, 2021

(51) Int. Cl.
*A61B 17/29* (2006.01)
*A61B 17/00* (2006.01)

(52) U.S. Cl.
CPC ...... *A61B 17/2909* (2013.01); *A61B 2017/00438* (2013.01); *A61B 2017/00477* (2013.01); *A61B 2017/2911* (2013.01); *A61B 2017/2912* (2013.01); *A61B 2017/2927* (2013.01)

(58) Field of Classification Search
CPC ...... A61B 17/2909; A61B 2017/00438; A61B 2017/00477; A61B 2017/2911; A61B 2017/2912; A61B 2017/2927; A61B 17/00234; A61B 34/71; A61B 2017/00323; A61B 2017/00424; A61B 2017/00738; A61B 2017/2904; A61B 2017/29048; A61B 2017/291; A61B 2017/2923; A61B 2017/2944; A61B 2017/294

See application file for complete search history.

(56) References Cited

U.S. PATENT DOCUMENTS

| | | | |
|---|---|---|---|
| 6,394,998 B1 | 5/2002 | Wallace et al. | |
| 10,631,886 B2 | 4/2020 | Lee et al. | |
| 10,709,467 B2 | 7/2020 | Lee et al. | |
| 2007/0208375 A1 | 9/2007 | Nishizawa et al. | |
| 2015/0150635 A1 | 6/2015 | Kilroy et al. | |
| 2018/0049842 A1* | 2/2018 | Bowles | A61B 34/71 |
| 2018/0110577 A1* | 4/2018 | Lee | A61B 34/71 |
| 2019/0105069 A1 | 4/2019 | Shelton, IV et al. | |
| 2019/0336230 A1 | 11/2019 | Awtar et al. | |
| 2020/0297445 A1 | 9/2020 | Lee et al. | |

FOREIGN PATENT DOCUMENTS

| | | |
|---|---|---|
| CN | 109674510 A | 4/2019 |
| JP | 1984-102587 | 6/1984 |
| JP | 08-000945 U | 6/1996 |
| JP | 2010-220786 A | 10/2010 |
| JP | 2017-510359 A | 4/2017 |

(Continued)

*Primary Examiner* — George J Ulsh
(74) *Attorney, Agent, or Firm* — Novick, Kim & Lee, PLLC; Sang Ho Lee

(57) ABSTRACT

The present disclosure relates to an instrument for surgery and, more specifically, to an instrument for surgery which can be manually operated in order to be used for laparoscopic surgery or various types of surgery.

20 Claims, 20 Drawing Sheets

(56) References Cited

FOREIGN PATENT DOCUMENTS

| KR | 10-1295396 B1 | 8/2013 |
| KR | 10-2016-0101538 A | 8/2016 |
| KR | 10-2017-0070675 A | 6/2017 |
| KR | 10-2018-0012259 A | 2/2018 |
| KR | 10-1968740 B1 | 4/2019 |

* cited by examiner

INSTRUMENT FOR SURGERY

TECHNICAL FIELD

The present disclosure relates to an instrument for surgery and, more specifically, to an instrument for surgery which may be manually operated for laparoscopic surgery or various other types of surgery.

BACKGROUND ART

Surgical operations refer to medical operations for curing disease by cutting, incising, or processing the skin, mucous membranes, or other tissue using medical instruments. In particular, open surgery, in which the skin of a surgical site is cut open to cure, shape, or remove an inside organ, causes problems such as bleeding, side effects, pain in patients, or scars. Therefore, as alternatives, a surgical operation, which is performed by forming a hole through the skin and inserting into the hole only a medical instrument such as a laparoscope, a surgical instrument, or a microscope for microsurgery, or a robotic surgical operation, have recently been favored.

Instruments for surgery are tools for performing an operation on a surgical site by handling an end tool provided on an end of a shaft inserted into a hole formed through the skin, and a surgeon may handle the end tool using a robotic arm or manually using a driving unit. Such an end tool of an instrument for surgery is configured to perform motions such as rotation, gripping, or cutting using a certain structure.

However, since instruments for surgery of the related art have unbendable end tools, it is difficult to access a surgical site and perform various surgical actions. In order to solve this problem, an instrument for surgery having a bendable end tool has been developed. However, the operation of a manipulation part for bending the end tool or performing a surgical action does not intuitively match the actual bending of the end tool or the actual surgical action, and thus for surgeons, it is difficult to intuitively handle the instrument for surgery and takes a long time to be able to skillfully use the instrument for surgery.

The above-described background art is technical information that the inventors obtained or learned when or while inventing the present disclosure, and may not be publicly disclosed before the filing of the present patent application.

DETAILED DESCRIPTION OF THE DISCLOSURE

Technical Problem

To solve the above-described problems, an object of the present disclosure is to provide an instrument for surgery configured to intuitively match motions of an end tool for bending or surgery with manipulations of a manipulation part. More particularly, to this end, the present disclosure provides an end tool having a plurality of degrees of freedom, a manipulation part configured to intuitively control the operation of the end tool, and a power transmission part configured to transmit driving force of the manipulation part to the end tool for operating the end tool according to manipulations of the manipulation part.

Technical Solution

An embodiment of the present disclosure provides an instrument for surgery, the instrument including: an end tool including a first jaw and a second jaw that are rotatable, the end tool being rotatable in at least two directions; a manipulation part configured to control rotation of the end tool in the at least two directions; a power transmission part connected to the manipulation part, the power transmission part including a first jaw wire that transmits rotation of the manipulation part to the first jaw and a second jaw wire that transmits rotation of the manipulation part to the second jaw; and a connecting part extending in a first direction (X axis), the connecting part being coupled to the end tool at an end portion thereof and coupled to the manipulation part at another end portion thereof so as to connect the manipulation part to the end tool, wherein the manipulation part includes: an actuation manipulation part configured to control actuation motion of the end tool; and a ring handle formed on an end portion of the actuation manipulation part, the ring handle including a fixed ring portion and a variable ring portion to receive a user's finger therein.

Other aspects, features, and advantages will become apparent and more readily appreciated from the accompanying drawings, claims, and detailed description.

Advantageous Effects of the Disclosure

According to the present disclosure, a direction in which a surgeon handles the manipulation part is intuitively identical to a direction in which the end tool is operated. Therefore, surgeons may conveniently perform surgery, and the accuracy, reliability, and speed of surgery may be improved.

BEST MODE

Figure 1A:
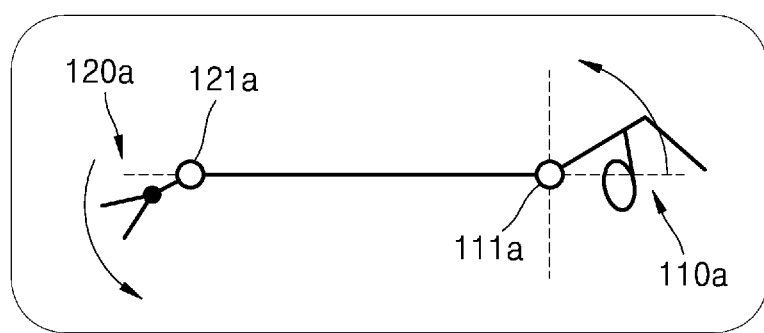
FIG. 1A is a schematic view illustrating a pitch motion of an instrument for surgery of the related art.

The present disclosure may include various embodiments and modifications, and particular embodiments thereof are illustrated in the drawings and will be described herein in detail. However, it will be understood that the present disclosure is not limited to the embodiments and includes all modifications, equivalents, and replacements within the idea and technical scope of the present disclosure. Moreover, detailed descriptions related to well-known functions or configurations will be omitted in order not to unnecessarily obscure subject matters of the present disclosure.

Although terms such as "first" and "second" may be used herein to describe various elements or components, these elements or components should not be limited by these terms. These terms are only used to distinguish one element or component from other elements or components.

The terminology used herein is for explaining specific embodiments only and is not intended to limit the present disclosure. As used herein, the singular forms "a," "an", and "the" are intended to include the plural forms as well, unless the context clearly indicates otherwise. It will be understood that terms such as "comprise," "include," and "have," when used herein, specify the presence of state features, integers, steps, operations, elements, components, or combinations thereof, but do not preclude the presence or addition of one or more other features, integers, steps, operations, elements, components, or combinations thereof.

Hereinafter, embodiments of the present disclosure will be described in detail with reference to the accompanying drawings. In the following description, like reference numerals denote like elements, and redundant descriptions thereof will be omitted.

In addition, it will be understood that various embodiments of the present disclosure may be interpreted or implemented in combination, and technical features of each embodiment may be interpreted or implemented in combination with technical features of other embodiments.

<First Embodiment of Instrument for Surgery>

An instrument for surgery of the present disclosure is characterized in that if a manipulation part is rotated in one direction for at least any one of pitch, yaw, and actuation motions, an end tool is rotated in intuitively the same direction as the direction in which the manipulation part is manipulated.

Figure 1B:
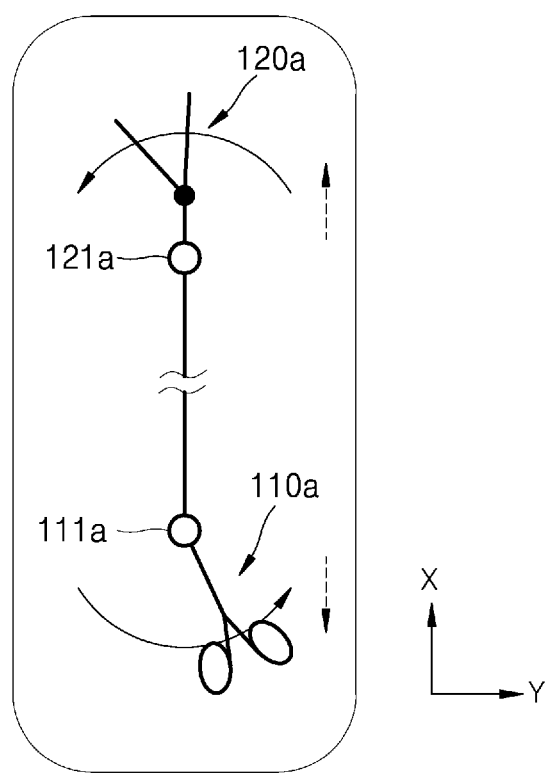
FIG. 1B is a schematic view illustrating a yaw motion of the instrument for surgery of the related art.

FIG. 1A is a schematic view illustrating pitch motion of an instrument for surgery of the related art, and FIG. 1B is a schematic view illustrating yaw motion of the instrument for surgery of the related art.

Referring to FIG. 1A, a pitch motion of the instrument for surgery of the related art is performed as follows. In a state in which an end tool 120a is in front of an end tool rotation center 121a and a manipulation part 110a is in back of a manipulation part rotation center 111a, if the manipulation part 110a is rotated clockwise, the end tool 120a is also rotated clockwise, and if the manipulation part 110a is rotated counterclockwise, the end tool 120a is also rotated counterclockwise. Referring to FIG. 1B, a yaw motion of the instrument for surgery of the related art is performed as follows. In a state in which the end tool 120a is in front of the end tool rotation center 121a and the manipulation part 110a is in back of the manipulation part rotation center 111a, if the manipulation part 110a is rotated clockwise, the end tool 120a is also rotated clockwise, and if the manipulation part 110a is rotated counterclockwise, the end tool 120a is also rotated counterclockwise. In this case, from the viewpoint of a horizontal direction of a user, when the user moves the manipulation part 110a to the left, the end tool 120a moves to the right, and when the user moves the manipulation part 110a to the right, the end tool 120a moves to the left. Consequently, since the manipulation direction of the user and the operation direction of the end tool are opposite each other, the user may make mistakes and have difficulty in manipulation.

Figure 1C:
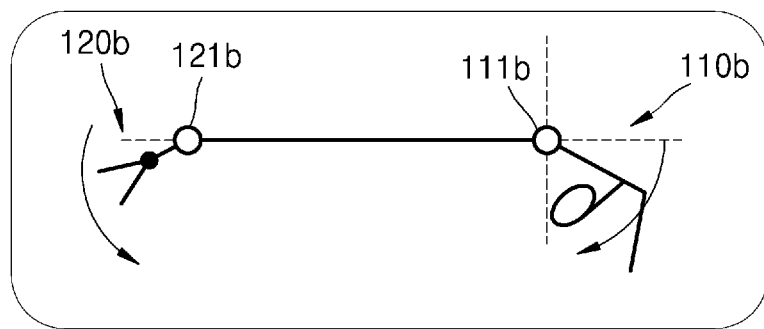
FIG. 1C is a schematic view illustrating a pitch motion of another instrument for surgery of the related art.
Figure 1D:
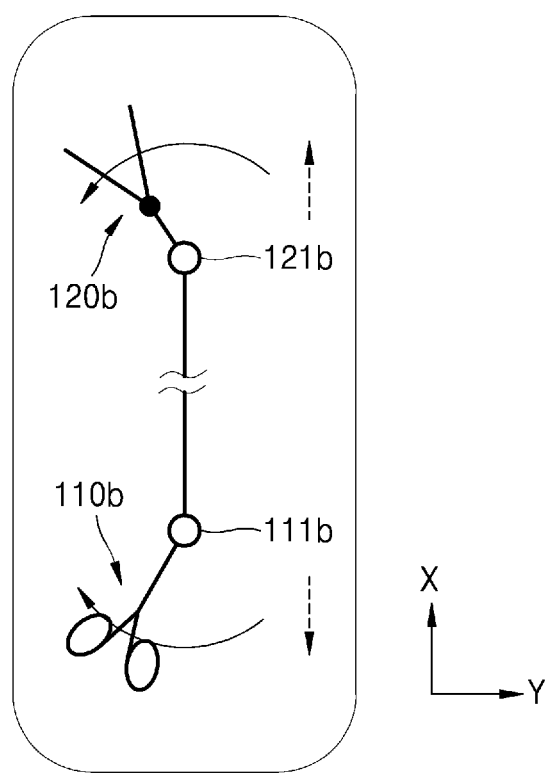
FIG. 1D is a schematic view illustrating a yaw motion of the other instrument for surgery of the related art.

FIG. 1C is a schematic view illustrating a pitch motion of another instrument for surgery of the related art, and FIG. 1D is a schematic view illustrating a yaw motion of the instrument for surgery of the related art.

Figure 1E:
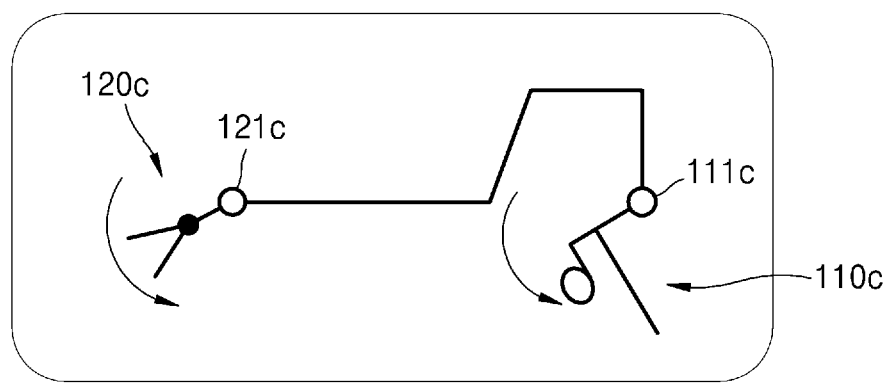
FIG. 1E is a schematic view illustrating a pitch motion of an instrument for surgery according to the present disclosure.
Figure 1F:
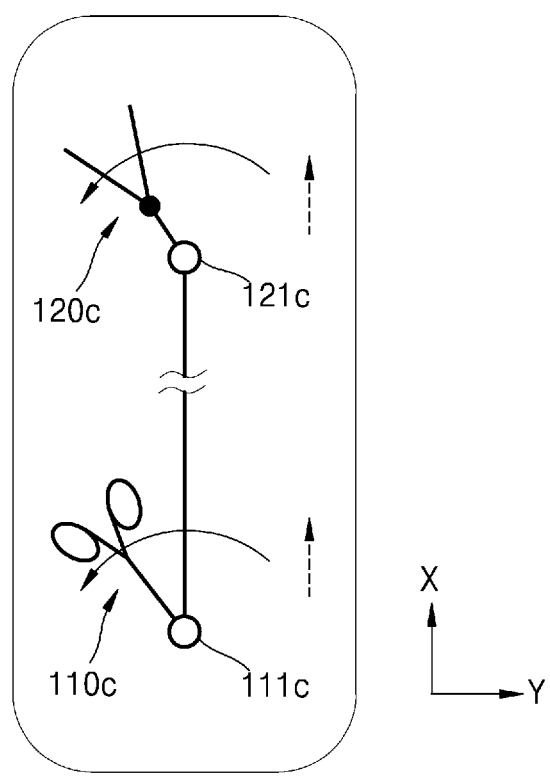
FIG. 1F is a schematic view illustrating a yaw motion of the instrument for surgery according to the present disclosure.

Referring to FIG. 1C, some instruments for surgery of the related art have a mirror-symmetric structure and perform a pitch motion as follows: in a state in which an end tool 120b is formed in front of an end tool rotation center 121b and an manipulation part 110b is formed in back of a manipulation part rotation center 111b, when the manipulation part 110b is rotated clockwise, the end tool 120b is rotated counterclockwise, and when the manipulation part 110b is rotated counterclockwise, the end tool 120b is rotated clockwise. In this case, from the viewpoint of the rotation directions of the manipulation part 110b and the end tool 120b, the direction in which a user rotates the manipulation part 110b is opposite the direction in which the end tool 120b is accordingly rotated. Consequently, the user may confuse manipulation directions, and the operation of a joint may not be intuitive, thereby causing mistakes. In addition, referring to FIG. 1D, a yaw motion is performed as follows. In a state in which the end tool 120b is in front of the end tool rotation center 121b and the manipulation part 110b is in back of the manipulation part rotation center 111b, if the manipulation part 110b is rotated clockwise, the end tool 120b is rotated counterclockwise, and if the manipulation part 110b is rotated counterclockwise, the end tool 120b is rotated clockwise. In this case, from the viewpoint of the rotation directions of the manipulation part 110b and the end tool 120b, the direction in which a user rotates the manipulation part 110b is opposite the direction in which the end tool 120b is accordingly rotated. Consequently, the user may confuse manipulation directions, and the operation of the joint may not be intuitive, thereby causing mistakes. As described above, when a user performs a pitch or yaw motion of an instrument for surgery of the related art, the manipulation direction of the user is not the same as the operation direction of an end tool from the viewpoint of the rotation directions or the horizontal direction. This is because an end tool and a manipulation part of an instrument for surgery of the related art have different joint structures. That is, the end tool is formed in front of the rotation center of the end tool, whereas the manipulation part is formed in back of the rotation center of the manipulation part. In order to address this problem, instruments for surgery according to embodiments of the present disclosure illustrated in FIGS. 1E and 1F are characterized in that an end tool 120c is provided in front of an end tool rotation center 121c and a manipulation part 110c is also provided in front of a manipulation part rotation center 111c, such that the operations of the manipulation part 110c and the end tool 120c are intuitively identical to each other. In other words, unlike the configuration example of the related art in which the manipulation part is adjacent to a user (i.e., distant from the end tool) based on a joint thereof as illustrated in FIGS. 1A, 1B, 1C, and 1D, the instruments for surgery according to the embodiments of the present disclosure illustrated in FIGS. 1E and 1F are configured such that at least a portion of the manipulation part may be more adjacent to the end tool based on a joint thereof (i.e., than the joint thereof is to the end tool) at at least a moment of manipulation.

In other words, in the case of an instrument for surgery of the related art as illustrated in FIGS. 1A, 1B, 1C, and 1D, since an end tool is located in front of a rotation center thereof but a manipulation part is located in back of a rotation center thereof, the end tool fixed at a rear side thereof and configured to be moved at a front side thereof is moved by the manipulation part fixed at a front side thereof and configured to be moved at a rear side thereof, and thus the structures of the manipulation part and the end tool are not intuitively identical to each other. Therefore, the manipulation of the manipulation part and the operation of the end tool are not identical to each other from the viewpoint of the horizontal direction or rotation directions, and thus a user may be confused and may not intuitively quickly manipulate the manipulation part, thereby making mistakes. However, in the case of the instruments for surgery according to the embodiments of the present disclosure, since each of the end tool and the manipulation part moves with respect to a rear rotation center thereof, it may be considered that the operations of the end tool and the manipulation part are structurally intuitively identical to each other. In other words, like the end tool having a portion movable based on the rear rotation center thereof, the manipulation part has a portion movable based on the rear rotation center thereof. Thus, it may be considered that the operations of the end tool and the manipulation part are structurally intuitively identical to each other. Consequently, a user may intuitively rapidly control the direction of the end tool, and the possibility that the user makes a mistake may be significantly reduced. A specific mechanism enabling this function will be described below.

Figure 2:
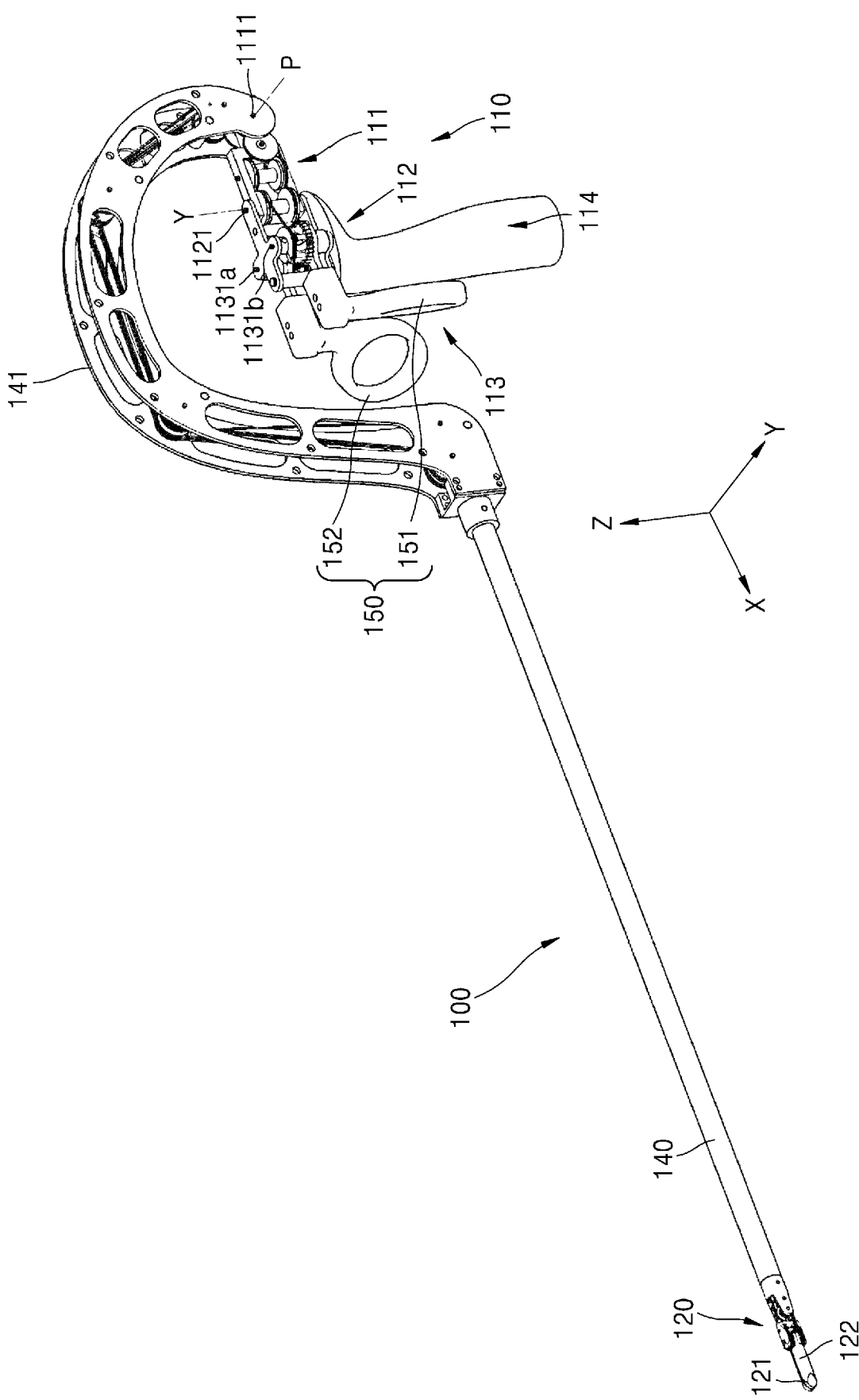
FIG. 2 is a perspective view illustrating an instrument for surgery according to a first embodiment of the present disclosure.
Figure 3:
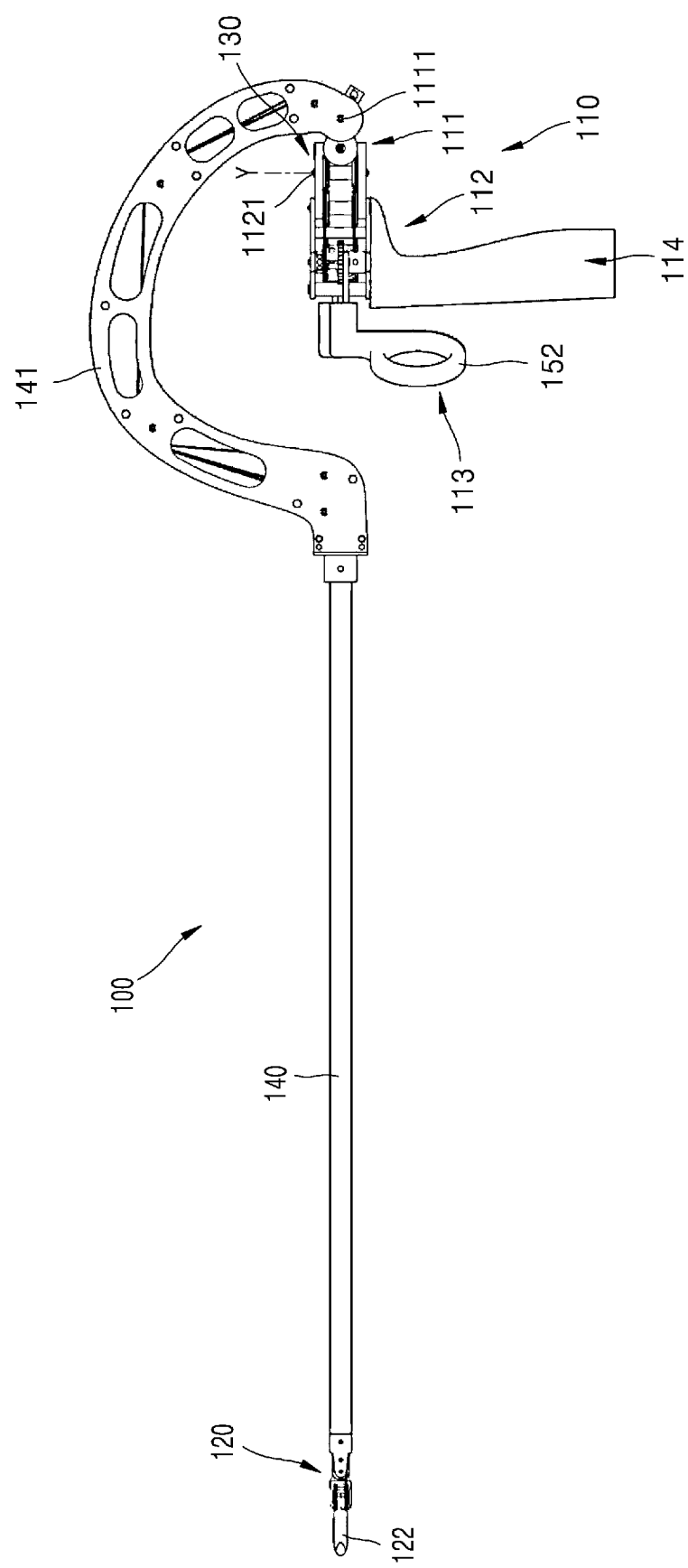
FIG. 3 is a side view illustrating the instrument for surgery shown in FIG. 2.

FIG. 2 is a perspective view illustrating an instrument for surgery according to a first embodiment of the present disclosure, and FIG. 3 is a side view illustrating the instrument for surgery shown in FIG. 2.

Referring to FIGS. 2, and 3, the instrument 100 for surgery according to the first embodiment of the present disclosure includes a manipulation part 110, an end tool 120, a power transmission part 130, a connecting part 140, and a ring handle 150.

Here, the connecting part 140 may have a hollow shaft shape accommodating at least one wire (described later). The manipulation part 110 may be coupled to one end portion of the connecting part 140, and the end tool 120 may be coupled to the other end portion of the connecting part 140 such that the manipulation part 110 and the end tool 120 may be connected through the connecting part 140. Here, the connecting part 140 of the instrument 100 for surgery according to the first embodiment of the present disclosure is characterized by having a bent part 141 on a side of the manipulation part 110. As described above, an end portion of the connecting part 140 located on a side of the manipulation part 110 is bent such that a pitch manipulation part 111, a yaw manipulation part 112, and an actuation manipulation part 113 may be located on or adjacent to an extension line of the end tool 120. From another perspective, it may be stated that at least portions of the pitch manipulation part 111 and the yaw manipulation part 112 is accommodated in a concave region formed by the bent part 141. Owning to the shape of the bent part 141, the shapes and operations of the manipulation part 110 and the end tool 120 may be more intuitively identical to each other.

In addition, a plane formed by the bent part 141 may be substantially the same as a pitch plane, that is, an XZ plane shown in FIG. 2. In this manner, since the bent part 141 is provided on the same plane as the XZ plane, interference between manipulation parts may be reduced. Alternatively, any other configuration of the end tool and the manipulation part may be possible in addition to the XZ plane configuration.

The manipulation part 110 is provided on one end portion of the connecting part 140 and has an interface such as a tweezers shape, a stick shape, or a lever shape that a surgeon may directly manipulate, such that if an surgeon manipulates the interface, the end tool 120 connected to the interface and inserted into the body of a patient may be operated for surgery. Although FIG. 2 illustrates that the manipulation part 110 has a handle shape configured to be rotated by inserting a finger thereinto, the idea of the present disclosure is not limited thereto. That is, the manipulation part 110 may have any shape as long as the end tool 120 is connected to the manipulation part 110 and manipulated using the manipulation part 110.

The end tool 120 is provided on the other end portion of the connecting part 140 and is configured to be moved for surgery in a state in which that end tool 120 is inserted into a surgical site. As an example of the end tool 120, a pair of jaws 121 and 122 for gripping may be used as illustrated in FIG. 2. However, the idea of the present disclosure is not limited thereto. That is, various devices for surgery may be used as the end tool 120. For example, a device such as a one-armed cauter may be used as the end tool 120. The end tool 120 is connected to the manipulation part 110 through the power transmission part 130 to receive a driving force of the manipulation part 110 through the power transmission part 130, thereby performing a necessary surgical motion such as gripping, cutting, or suturing.

Herein, the end tool 120 of the instrument 100 for surgery of the first embodiment of the present disclosure is configured to rotate in at least two directions. For example, the end tool 120 may be capable of pitch motion around a Y axis of FIG. 2 and yaw motion and actuation motion around a Z axis of FIG. 2.

In the present disclosure, pitch, yaw, and actuation motions are defined as follows.

First, the pitch motion refers to upward and downward rotations of the end tool 120 with respect to an extension direction (the direction of an X axis in FIG. 2) of the connecting part 140, that is, rotation of the end tool 120 around the Y axis in FIG. 2. In other words, the pitch motion refers to upward and downward rotations of the end tool 120, which extends from the connecting part 140 in the extension direction (the X-axis direction in FIG. 2) of the connecting part 140, around the Y axis with respect to the connecting part 140. Next, the yaw motion refers to leftward and rightward rotations of the end tool 120 with respect to the extension direction (the X-axis direction in FIG. 2) of the connecting part 140, that is, rotation of the end tool 120 around the Z axis in FIG. 2. In other words, the yaw motion refers to leftward and rightward rotations of the end tool 120, which extends from the connecting part 140 in the extension direction (the X-axis direction in FIG. 2) of the connecting part 140, around the Z axis with respect to the connecting part 140. That is, the yaw motion refers to a motion in which the two jaws 121 and 122 of the end tool 120 are rotated around the Z axis in the same direction. In addition, the actuation motion refers to a motion in which the end tool 120 rotates around the same rotation axis as the yaw motion but the two jaws 121 and 122 rotate in opposite directions to move close to each other or away from each other. That is, the actuation motion refers to a motion in which the two jaws 121 and 122 rotate around the Z axis in opposite directions.

The power transmission part 130 may connect the manipulation part 110 and the end tool 120 to each other and transmit a driving force of the manipulation part 110 to the end tool 120. The power transmission part 130 may include a plurality of wires, pulleys, links, nodes, and gears. According to the embodiment of the present disclosure, the power transmission part 130 of the instrument 100 for surgery may include a pitch wire 130P, a first jaw wire 130J1, and a second jaw wire 130J2.

The ring handle 150 includes a first ring handle 151 and a second ring handle 152, and each of the ring handles 151 and 152 includes a fixed ring portion 153 and a variable ring portion 154. In an embodiment of the present disclosure, the instrument 100 for surgery includes the variable ring portions 154 for adjusting the sizes of holes of rings according to the sizes of fingers of a user such that the fingers of the user may be fitted into or tightly coupled to the ring handle 150, thereby improving convenience in manipulation for users. This will be described later in more detail.

Hereinafter, parts of the instrument 100 for surgery shown in FIG. 2 such as the manipulation part 110, the end tool 120, and the power transmission part 130 will be described in more detail.

Figure 4:
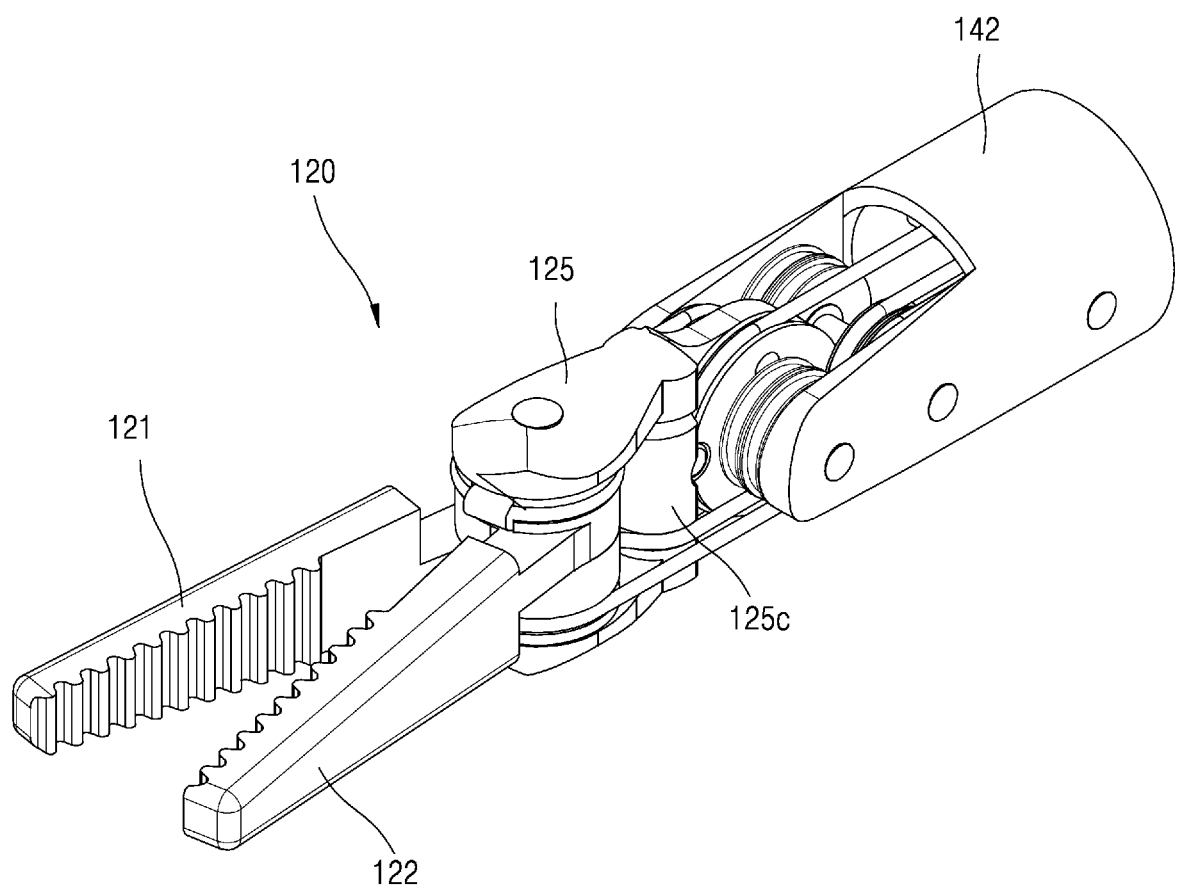
FIGS. 4 and 5 are perspective views illustrating an end tool of the instrument for surgery shown in FIG. 2.
Figure 5:
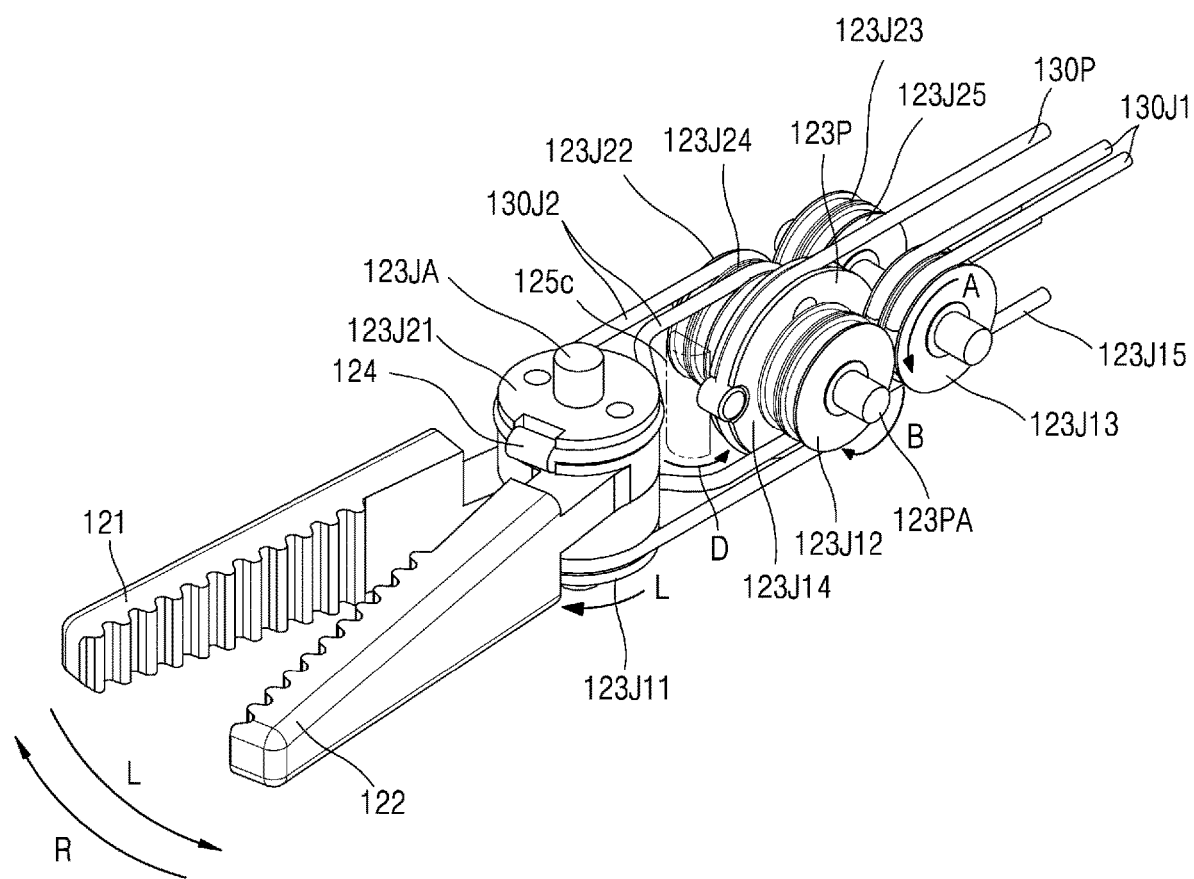
Figure 6:
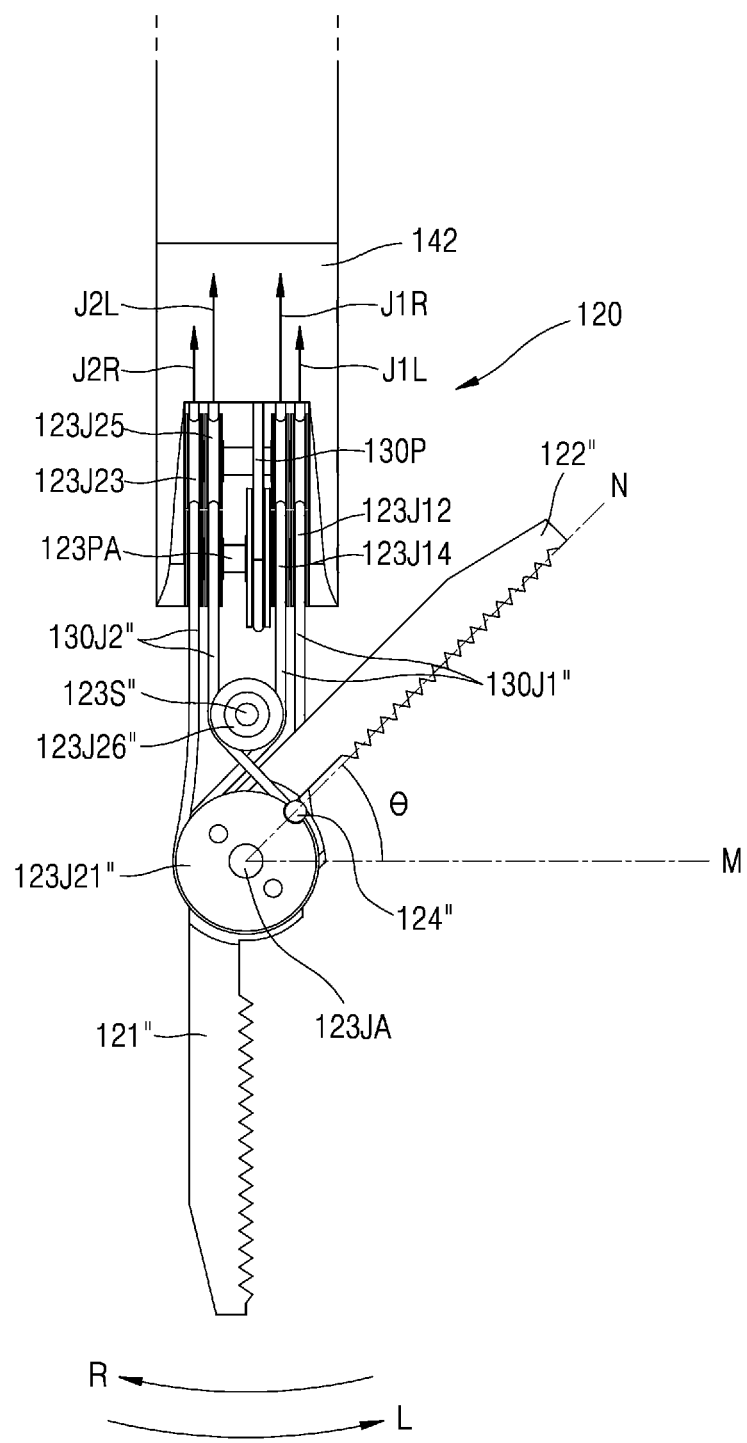
FIG. 6 is a plan view illustrating the end tool of the instrument for surgery shown in FIG. 2.

FIGS. 4 and 5 are perspective views illustrating the end tool of the instrument for surgery shown in FIG. 2, and FIG. 6 is a plan view illustrating the end tool of the instrument for surgery shown in FIG. 2.

Referring to FIGS. 4, 5 and 6, the end the end tool 120 of the first embodiment of the present disclosure includes a pair of jaws 121 and 122, that is, a first jaw 121 and a second jaw 122 for gripping motion. In addition, the end tool 120 includes: a J11 pulley 123J11, a J12 pulley 123J12, a J13 pulley 123J13, a J14 pulley 123J14, and a J15 pulley 123J15 that are related to the rotation motion of the first jaw 121; and a J21 pulley 123J21, a J22 pulley 123J22, a J23 pulley 123J23, a J24 pulley 123J24, and a J25 pulley 123J25 that are related to the rotation motion of the second jaw 122. In this case, the first jaw 121, the J11 pulley 123J11, the J12 pulley 123J12, the J14 pulley 123J14, the second jaw 122, the J21 pulley 123J21, the J22 pulley 123J22, and the J24 pulley 123J24 may be configured to rotate around an end tool pitch rotation shaft 123PA.

In addition, a connecting part hub 142 is provided on an end portion of the connecting part 140 coupled to the end tool 120. The J12 pulley 123J12, the J13 pulley 123J13, the J14 pulley 123J14, the J15 pulley 123J15, the J22 pulley 123J22, the J23 pulley 123J23, the J24 pulley 123J24, and the J25 pulley 123J25 are connected to the connecting part hub 142.

Although it is illustrated that pulleys facing each other are parallel to each other, the idea of the present disclosure is not limited thereto. That is, the pulleys may have various positions and sizes suitable for the configuration of the end tool.

The J11 pulley 123J11 and the J21 pulley 123J21 face each other and rotate independently around a jaw rotation shaft 123JA. Here, the first jaw 121 may be fixedly coupled to the J11 pulley 123J11 so as to be rotated together with the J11 pulley 123J11, and the second jaw 122 may be fixedly coupled to the J21 pulley 123J21 so as to be rotated together with the J21 pulley 123J21. Yaw and actuation motions of the end tool 120 are performed as according to rotations of the J11 pulley 123J11 and the J21 pulley 123J21. That is, yaw motion is performed when the J11 pulley 123J11 and the J21 pulley 123J21 are rotated in the same direction, and actuation motion is performed when the J11 pulley 123J11 and the J21 pulley 123J21 are rotated in opposite directions.

In addition, a J16 pulley 123J16 and a J26 pulley 123J26 may be additionally provided as auxiliary pulleys on a side of the J11 pulley 123J11 and the J21 pulley 123J21, and the auxiliary pulleys may be rotatable on an auxiliary pulley shaft 123S. Although it is illustrated that the J16 pulley 123J16 and the J26 pulley 123J26 are configured to rotate on the single auxiliary pulley shaft 123S, the auxiliary pulleys may be configured to rotate on separate shafts, respectively. In other words, the J16 pulley 123J16 being an auxiliary pulley may be placed between the J11 pulley 123J11 and the J12 pulley 123J12/the J14 pulley 123J14. In addition, the J26 pulley 123J26 being an auxiliary pulley may be placed between the J21 pulley 123J21 and the J22 pulley 123J22/the J24 pulley 123J24. The auxiliary pulleys will be described later in more detail.

Elements related to rotation of the J11 pulley 123J11 will be described below.

The J12 pulley 123J12 and the J14 pulley 123J14 are placed to face each other at a side of the J11 pulley 123J11. In this case, the J12 pulley 123J12 and the J14 pulley 123J14 are independently rotatable about the end tool pitch rotation shaft 123PA. In addition, the J13 pulley 123J13 and the J15 pulley 123J15 are placed to face each other respectively at sides of the J12 pulley 123J12 and the J14 pulley 123J14. Here, the J13 pulley 123J13 and the J15 pulley 123J15 are independently rotatable around the Y-axis direction. Although it is illustrated that all of the J12 pulley 123J12, the J13 pulley 123J13, the J14 pulley 123J14, and the J15 pulley 123J15 are rotatable around the Y-axis direction, the idea of the present disclosure is not limited thereto, and the rotating axes of the respective pulleys may be oriented in various directions according to configurations thereof.

The first jaw wire 130J1 may be sequentially wound to make contact with at least portions of the J13 pulley 123J13, the J12 pulley 123J12, the J11 pulley 123J11, the J16 pulley 123J16, the J14 pulley 123J14, and the J15 pulley 123J15, and the first jaw wire 130J1 may move along the pulleys while rotating the pulleys.

Thus, when the first jaw wire 130J1 is pulled in the direction of an arrow J1R in FIG. 6, the first jaw wire 130J1 rotates the J15 pulley 123J15, the J14 pulley 123J14, the J16 pulley 123J16, the J11 pulley 123J11, the J12 pulley 123J12, and the J13 pulley 123J13. At this time, as the J11 pulley 123J11 is rotated in the direction of an arrow R in FIG. 6, the J11 pulley 123J11 rotates the first jaw 121.

On the other hand, when the first jaw wire 130J1 is pulled in the direction of an arrow J1L in FIG. 6, the first jaw wire 130J1 rotates the J13 pulley 123J13, the J12 pulley 123J12, the J11 pulley 123J11, the J16 pulley 123J16, the J14 pulley 123J14, and the J15 pulley 123J15. At this time, as the J11 pulley 123J11 is rotated in the direction of an arrow L in FIG. 6, the J11 pulley 123J11 rotates the first jaw 121.

Hereinafter, the auxiliary pulleys 123J16 and 123J26 will be described in more detail.

The auxiliary pulleys 123J16 and 123J26 may be in contact with the first jaw wire 130J1 and the second jaw wire 130J2, thereby changing paths of the first jaw wire 130J1 and the second jaw wire 130J2 to some degree and extending the rotation radii of the first jaw 121 and the second jaw 122. That is, according to the embodiment of the present disclosure, the auxiliary pulleys 123J16 and 123J26 are additionally provided such that the maximum rotation angle may be increased by θ as illustrated in FIG. 6.

This allows the two jaws of the end tool 120 to move away from each other for actuation motion in a state in which the two jaws are rotated together by 90° in yaw motion in the direction L. That is, this is because it is possible to further rotate the second jaw 122 by an additional angle θ as illustrated in FIG. 6. Similarly, actuation motion is also possible in a state in which the two jaws are rotated in yaw motion in the direction R. In other words, owing to the auxiliary pulleys 123J16 and 123J26, the range of yaw motion in which actuation motion is possible may be increased. This will now be described in more detail.

In detail, in the instrument 100 for surgery according to the embodiment of the present disclosure, the J16 pulley 123J16 and the J26 pulley 123J26 are additionally arranged as auxiliary pulleys at a side of the J11 pulley 123J11 and the J21 pulley 123J21. In this manner, since the J16 pulley 123J16 and the J26 pulley 123J26 are arranged to change the paths of the first jaw wire 130J1 and the second jaw wire 130J2 to some degree and thus to change tangential directions of the first jaw wire 130J1 and the second jaw wire 130J2, a fixation coupling part of the second jaw wire 130J2 and the J21 pulley 123J21 may be rotated up to a line N of FIG. 6. That is, the fixation coupling part of the second jaw wire 130J2 and the J21 pulley 123J21 may be rotated until the coupling part is located on a common internal tangent of the J21 pulley 123J21 and the J26 pulley 123J26. Similarly, a coupling part of the first jaw wire 130J1 and the J11 pulley 123J11 may be rotated until the coupling part is located on an common internal tangent of the J11 pulley 123J11 and the J16 pulley 123J16, thereby extending the range of rotation in the direction R.

In this manner, according to the present disclosure, the rotation radii of the first jaw 121 and the second jaw 122 may be increased, thereby obtaining an effect of increasing the range of yaw motion in which actuation motion is normally performed for opening and closing.

Next, elements relating to the rotation of the J21 pulley 123J21 will be described.

The J22 pulley 123J22 and the J24 pulley 123J24 are placed to face each other at a side of the J21 pulley 123J21. Here, the J22 pulley 123J22 and the J24 pulley 123J24 are independently rotatable around the end tool pitch rotation shaft 123PA. In addition, the J23 pulley 123J23 and the J25 pulley 123J25 are placed to face each other at a side of the J22 pulley 123J22 and the J24 pulley 123J24. Here, the J23 pulley 123J23 and the J25 pulley 123J25 are independently rotatable around the Y-axis direction. Although it is illustrated that all of the J22 pulley 123J22, the J23 pulley 123J23, the J24 pulley 123J24, and the J25 pulley 123J25 are rotatable around the Y-axis direction, the idea of the present disclosure is not limited thereto, and the rotating axes of the respective pulleys may be oriented in various directions according to configurations thereof.

The second jaw wire 130J2 may be sequentially wound to make contact with at least portions of the J23 pulley 123J23, the J22 pulley 123J22, the J21 pulley 123J21, the J26 pulley 123J26, the J24 pulley 123J24, and the J25 pulley 123J25, and the second jaw wire 130J2 may move along the pulleys while rotating the pulleys.

Therefore, when the second jaw wire 130J2 is pulled in the direction of an arrow J2R of FIG. 6, the second jaw wire 130J2 rotates the J23 pulley 123J23, the J22 pulley 123J22, the J21 pulley 123J21, the J26 pulley 123J26, the J24 pulley 123J24, and the J25 pulley 123J25. At this time, as the J21 pulley 123J21 is rotated in the direction of the arrow R of FIG. 6, the J21 pulley 123J21 rotates the second jaw 122.

On the other hand, when the second jaw wire 130J2 is pulled in the direction of an arrow J2L of FIG. 6, the second jaw wire 130J2 rotates the J25 pulley 123J25, the J24 pulley 123J24, the J26 pulley 123J26, the J21 pulley 123J21, the J22 pulley 123J22, and the J23 pulley 123J23. At this time, as the J21 pulley 123J21 is rotated in the direction of the arrow L of FIG. 6, the J21 pulley rotates the second jaw 122.

In addition, if an end portion of the first jaw wire 130J1 is pulled in the direction of the arrow J1R of FIG. 6, and at the same time the other end portion of the first jaw wire 130J1 is pulled in the direction of the arrow J1L of FIG. 6 (that is, if both end portions of the first jaw wire 130J1 are pulled), since the first jaw wire 130J1 is wound around lower portions of the J12 pulley 123J12 and the J14 pulley 123J14 that are rotatable around the end tool pitch rotation shaft 123PA as shown in FIG. 5, the J11 pulley 123J11 to which the first jaw wire 130J1 is fixedly coupled, the first jaw 121, the jaw rotation shaft 123JA, and an end tool hub 123a, and the second jaw 122 connected thereto are all rotated counterclockwise around the end tool pitch rotation shaft 123PA, and as a result, the end tool 120 is rotated downward in pitch motion. At this time, since the second jaw 122 and the second jaw wire 130J2 fixedly coupled to the second jaw 122 is wound around upper portions of the J22 pulley 123J22 and the J24 pulley 123J24 that are rotatable around the end tool pitch rotation shaft 123PA, both end portions of the second jaw wire 130J2 are respectively moved in directions opposite the directions of the arrows J2L and J2R.

In contract, if an end portion of the second jaw wire 130J2 is pulled in the direction of the arrow J2R of FIG. 6, and at the same time the other end portion of the second jaw wire 130J2 is pulled in the direction of the arrow J2L of FIG. 6, since the second jaw wire 130J2 is wound around the upper portions of the J22 pulley 123J22 and the J24 pulley 123J24 that are rotatable around the end tool pitch rotation shaft 123PA as shown in FIG. 5, the J21 pulley 123J21 to which the second jaw wire 130J1 is fixedly coupled, the second jaw 122, the jaw rotation shaft 123JA, and the end tool hub 123a, and the first jaw 121 connected thereto are all rotated clockwise around the end tool pitch rotation shaft 123PA, and as a result, the end tool 120 is rotated upward in pitch motion. At this time, since the first jaw 121 and the first jaw wire 130J1 fixedly coupled to the first jaw 121 are wound around the lower portions of the J12 pulley 123J12 and the J14 pulley 123J14 that are rotatable around the end tool pitch rotation shaft 123PA, both end portions of the first jaw wire 130J1 are respectively moved in directions opposite the directions of the arrows J1L and J1R.

In addition, the end tool 120 of the instrument 100b for surgery may further include a pitch pulley 123P, the manipulation part 110 may further include a pitch wire end pulley 115P, and the power transmission part 130 may further include the pitch wire 130P. In detail, the pitch pulley 123P of the end tool 120 may be rotatable about the end tool pitch rotation shaft 123PA and may be fixedly coupled to the end tool hub 123a. In addition, a pitch pulley of the manipulation part may be rotatable about a pitch rotation shaft and may be fixedly coupled to a pitch manipulation part (not shown). In addition, the pitch wire 130P may connect the pitch pulley 123P of the end tool 120 to the pitch pulley of the manipulation part.

Thus, if a user rotates a first handle 114 around a pitch rotation shaft 1111 while holding the first handle 114 of the manipulation part 110, a pitch pulley coupled to the first handle 114 is rotated around the pitch rotation shaft 1111, and the rotation of the pitch pulley is transmitted to the pitch pulley 123P of the end tool 120 through the pitch wire 130P to rotate the pitch pulley 123P. As a result, the end tool 120 is rotated, and a pitch motion is performed.

That is, since the instrument 100 for surgery according to the first embodiment of the present disclosure includes the pitch pulley 123P of the end tool 120, the pitch wire end pulley 115P of the manipulation part 110, and the pitch wire 130P of the power transmission part 130, a pitch motion driving force of the pitch manipulation part 111 may be more completely transmitted to the end tool 120, and thus reliability of motion may be improved.

(Manipulation Part)

Figure 7:
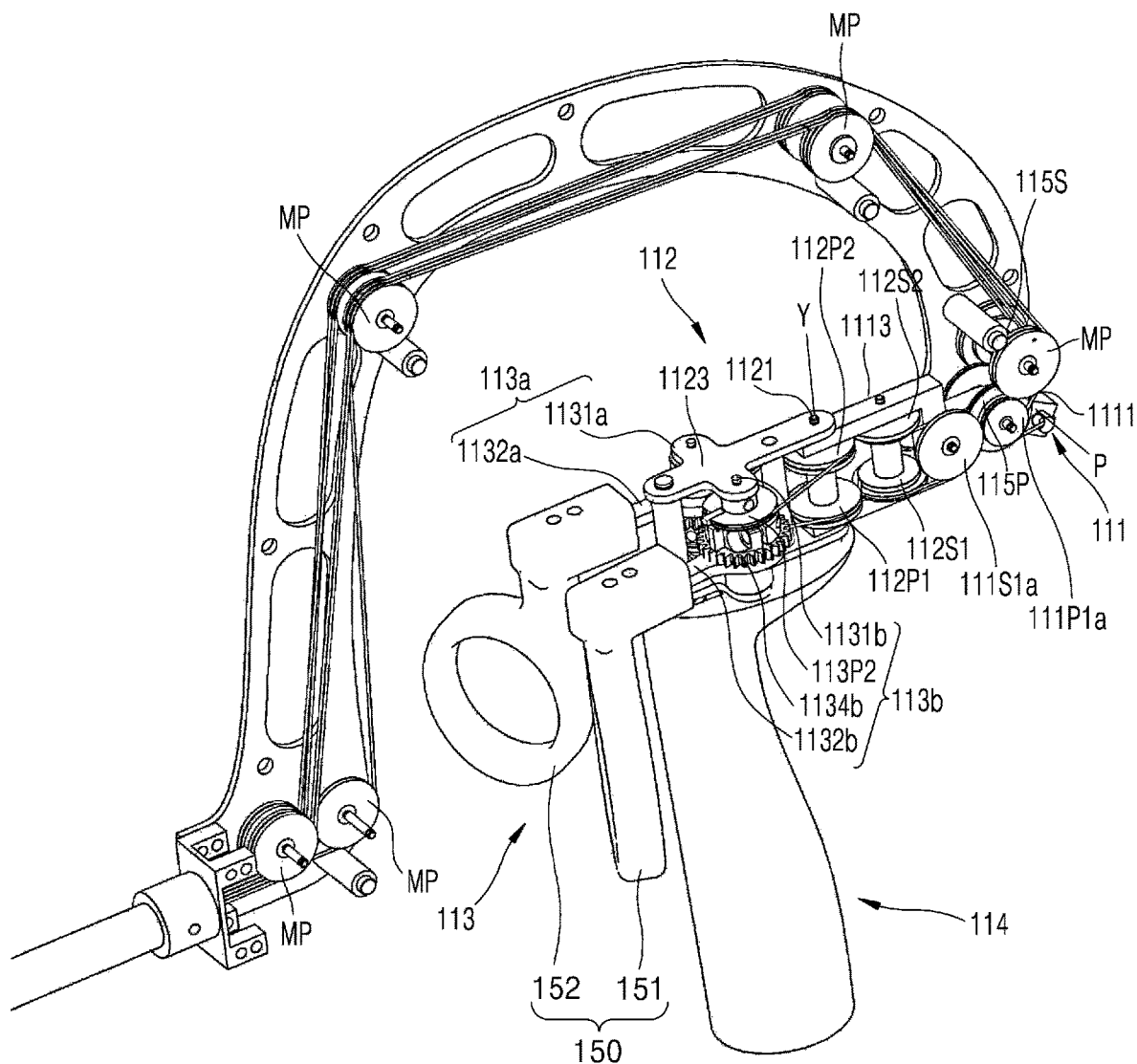
FIGS. 7 and 8 are perspective views illustrating a manipulation part of the instrument for surgery shown in FIG. 2.
Figure 8:
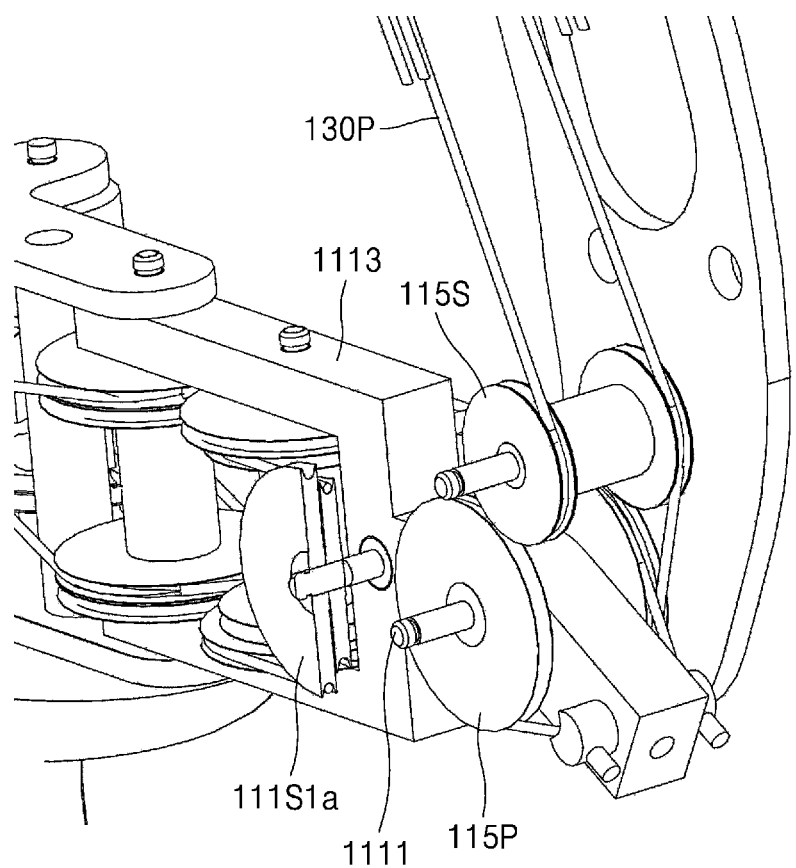

FIG. 7 is a perspective view illustrating the manipulation part of the instrument for surgery shown in FIG. 2, and FIG. 8 is a rear perspective view illustrating the instrument for surgery shown in FIG. 2.

Referring to FIG. 2 to FIG. 8, the manipulation part 110 of the instrument 100 for surgery includes the first handle 114 which a user may grip, the actuation manipulation part 113 configured to control actuation motion of the end tool 120, the yaw manipulation part 112 configured to control yaw motion of the end tool 120, and the pitch manipulation part 111 configured to control pitch motion of the end tool 120. In addition, the manipulation part 110 further includes the ring handle 150.

First, an example operation of the instrument 100 for surgery shown in FIG. 2 will be described. In a state in which a user holds the first handle 114 with his/her palm, the user may perform a pitch motion by rotating the first handle 114 around the Y axis (that is, around the pitch rotation shaft 1111) and a yaw motion by rotating the first handle 114 around the Z axis (that is, around a yaw rotation shaft 1121). In addition, in a state in which the user inserts his/her thumb and index finger in the ring handle 150 formed on an end of the actuation manipulation part 113, the user may rotate the actuation manipulation part 113 to perform an actuation motion.

Here, when the manipulation part 110 of the instrument 100 for surgery is rotated in a direction with respect to the connecting part 140, the end tool 120 is rotated intuitively in the same direction as the direction in which the manipulation part 110 is manipulated. In other words, if the first handle 114 of the manipulation part 110 is rotated in a certain direction, the end tool 120 is also rotated intuitively in the same direction as the certain direction, and thus a pitch motion or a yaw motion is performed. Here, the expression "intuitively in the same direction" may be used to denote that the direction in which a finger of a user holding the manipulation part 110 is moved is substantially the same as the direction in which a distal end portion of the end tool 120 is moved. The expression "intuitively in same direction" may not refer to completely in the same direction in a three-dimensional coordinate system. For example, it may be understood that the expression refers to sameness to the following extend: if a finger of a user is moved leftward, the distal end portion of the end tool 120 is also be moved leftward, and if the finger of the user is moved downward, the distal end portion of the end tool 120 is also moved downward.

To this end, in the instrument 100 for surgery of the first embodiment of the present disclosure, the manipulation part 110 and the end tool 120 are provided in the same direction with respect to a plane perpendicular to an extension axis (the X axis) of the connecting part 140. That is, when viewed based on a YZ plane of FIG. 2, the manipulation part 110 extends in a positive (+) X-axis direction, and the end tool 120 also extends in the positive (+) X-axis direction. In other words, it may be stated that the formation direction of the end tool 120 on an end portion of the connecting part 140 is the same as the formation direction of the manipulation part 110 on the other end portion of the connecting part 140 based on the YZ plane. Furthermore, in other words, it may be stated that the manipulation part 110 is located in a direction away from the body of a user holding the manipulation part 110, that is, in a direction in which the end tool 120 is provided. That is, in the case of parts such as the first handle 114 and actuation rotation parts 1132*a* and 1132*b* which a user holds and moves for actuation, yaw, and pitch motions, each moving portion extends from the rotation center of a corresponding joint for the motions in the positive (+) X-axis direction. In this manner, the manipulation part 110 may be configured like the end tool 120 in which each moving portion extends from the rotation center of a corresponding joint for the motions in the positive (+) X-axis direction, and as described with reference to FIG. 1, a manipulation direction of a user may be identical to an operation direction of the end tool from the viewpoint of rotation directions and leftward and rightward directions. As a result, intuitively the same manipulation may be performed.

In detail, in the case of an instrument for surgery of the related art, a direction in which a user manipulates a manipulation part is different from a direction in which the end tool is actually operated, that is, intuitively different from the direction in which the end tool is actually operated. Thus, surgeons may not easily intuitively manipulate the instrument for surgery and may spend a long time to learn a skill of operating the end tool in desired directions. In some cases, patients may suffer from malfunctions.

In order to solve such problems, the instrument 100 for surgery of the first embodiment of the present disclosure is configured such that the manipulation direction of the manipulation part 110 and the operation direction of the end tool 120 are intuitively identical to each other. To this end, the manipulation part 110 is configured like the end tool 120. That is, in the manipulation part 110, portions that are actually moved for actuation, yaw, and pitch motions extend respectively from rotation centers of corresponding joints in the positive (+) X-axis direction. This will now be described in more detail.

The first handle 114 may be configured such that a user may grip the first handle 114 with his/her hand. In particular, a user may grip the first handle 114 by holding around the first handle 114 with his/her palm. In addition, the actuation manipulation part 113 and the yaw manipulation part 112 are provided above the first handle 114, and the pitch manipulation part 111 is provided at a side of the yaw manipulation part 112. In addition, another end portion of the pitch manipulation part 111 is connected to the bent part 141 of the connecting part 140.

The actuation manipulation part 113 includes a first actuation manipulation part 113*a* and a second actuation manipulation part 113*b*. The first actuation manipulation part 113*a* includes a first actuation rotation shaft 1131*a*, a first actuation rotation part 1132*a*, a first actuation pulley 113P1, and a first actuation gear 1134*a*. The second actuation manipulation part 113*b* includes a second actuation rotation shaft 1131*b*, a second actuation rotation part 1132*b*, a second actuation pulley 113P2, and a second actuation gear 1134*b*. Here, the first ring handle 151 and the second ring handle 152 may be further formed on ends of the first and second actuation rotation parts 1132*a* and 1132*b* and may function as second handles.

Here, the actuation rotation shafts 1131*a* and 1131*b* may make a predetermined angle with an XY plane on which the connecting part 140 is located. For example, the actuation rotation shafts 1131*a* and 1131*b* may be parallel with the Z axis. In this state, if the pitch manipulation part 111 or the yaw manipulation part 112 is rotated, the coordinate system of the actuation manipulation part 113 may be relatively varied. However, the idea of the present disclosure is not limited thereto, and the actuation rotation shafts 1131*a* and 1131*b* may be oriented in various directions according to ergonomic designs for the hand structure of a user holding the actuation manipulation part 113.

In addition, the first actuation rotation part 1132a, the first actuation pulley 113P1, and the first actuation gear 1134a may be fixedly coupled to each other so as to be rotated together around the first actuation rotation shaft 1131a. Here, the first actuation pulley 113P1 may include a single pulley or two pulleys fixedly coupled to each other.

Similarly, the second actuation rotation part 1132b, the second actuation pulley 113P2, and the second actuation gear 1134b may be fixedly coupled to each other so as to be rotated together around the second actuation rotation shaft 1131b. Here, the second actuation pulley 113P2 may include a single pulley or two pulleys fixedly coupled to each other.

Here, the first actuation gear 1134a and the second actuation gear 1134b may be engaged with each other, and thus if one of the first and second actuation gears 1134a and 1134b is rotated, the first and second actuation gears 1134a and 1134b may be rotated together in opposite directions.

The yaw manipulation part 112 may include a yaw rotation shaft 1121, a first jaw yaw pulley 112P1, a second jaw yaw pulley 112P2, and a yaw frame 1123. In addition, the yaw manipulation part 112 may further include a first jaw yaw auxiliary pulley 112S1 provided on a side of the first jaw yaw pulley 112P1, and a second jaw yaw auxiliary pulley 112S2 provided on a side of the second jaw yaw pulley 112P2. Here, the first jaw yaw auxiliary pulley 112S1 and the second jaw yaw auxiliary pulley 112S2 may be coupled to a pitch frame 1113 (described later).

In the drawings, it is illustrated that the yaw manipulation part 112 includes the first jaw yaw pulley 112P1 and the second jaw yaw pulley 112P2, and each of the first jaw yaw pulley 112P1 and the second jaw yaw pulley 112P2 includes two pulleys facing each other and independently rotatable. However, the idea of the present disclosure is not limited thereto. That is, according to the configuration of the yaw manipulation part 112, the yaw manipulation part 112 may include one or more pulleys having the same diameter or different diameters.

Specifically, the yaw rotation shaft 1121 is provided on a side of the actuation manipulation part 113 above the first handle 114. In this case, the first handle 114 is rotatable around the yaw rotation shaft 1121.

Here, the yaw rotation shaft 1121 may make a predetermined angle with the XY plane in which the connecting part 140 is provided. For example, the yaw rotation shaft 1121 may be oriented in a direction parallel to the Z axis, and in this state, if the pitch manipulation part 111 is rotated, the coordinate system of the yaw rotation shaft 1121 may be relatively varied as described above. However, the idea of the present disclosure is not limited thereto, and the yaw rotation shaft 1121 may be oriented in various directions according to ergonomic designs for the hand structure of a user holding the manipulation part 110.

In addition, the first jaw yaw pulley 112P1 and the second jaw yaw pulley 112P2 are coupled to the yaw rotation shaft 1121 such that the first jaw yaw pulley 112P1 and the second jaw yaw pulley 112P2 may be rotated on the yaw rotation shaft 1121. In addition, the first jaw wire 130J1 may be wound around the first jaw yaw pulley 112P1, and the second jaw wire 130J2 may be wound around the second jaw yaw pulley 112P2. In this case, each of the first jaw yaw pulley 112P1 and the second jaw yaw pulley 112P2 may include two pulleys facing each other and independently rotatable. Therefore, an inward wire and an outward wire may be respectively wound around separate pulleys and thus may not interfere with each other.

The yaw frame 1123 connects the first handle 114, the yaw rotation shaft 1121, the first actuation rotation shaft 1131a, and the second actuation rotation shaft 1131b such that the first handle 114, the yaw manipulation part 112, and the actuation manipulation part 113 may be rotated together around the yaw rotation shaft 1121.

The pitch manipulation part 111 may include the pitch rotation shaft 1111, a first jaw pitch pulley-a 111P1a, a first jaw pitch pulley-b 111P1b, a second jaw pitch pulley-a 111P2a, a second jaw pitch pulley-b 111P2b, and the pitch frame 1113. In addition, the pitch manipulation part 111 may further include a first jaw pitch auxiliary pulley-a 111S 1a provided at a side of the first jaw pitch pulley-a 111P1a, a first jaw pitch auxiliary pulley-b 111S 1b provided at a side of the first jaw pitch pulley-b 111P1b, a second jaw pitch auxiliary pulley-a 111S2a provided at a side of the second jaw pitch pulley-a 111P2a, and a second jaw pitch auxiliary pulley-b 111S2b provided at a side of the second jaw pitch pulley-b 111P2b. The pitch manipulation part 111 is connected to a bent part 141 of a connecting part 140 through the pitch rotation shaft 1111.

In detail, the pitch frame 1113 serves as a base frame of the pitch manipulation part 111, and the yaw rotation shaft 1121 is rotatably coupled to an end portion of the pitch frame 1113. That is, the yaw frame 1123 is rotatable around the yaw rotation shaft 1121 with respect to the pitch frame 1113.

As described above, the yaw frame 1123 connects the first handle 114, the yaw rotation shaft 1121, the first actuation rotation shaft 1131a, and the second actuation rotation shaft 1131b to each other, and is also connected to the pitch frame 1113. Therefore, if the pitch frame 1113 is rotated around the pitch rotation shaft 1111, the yaw frame 1123, the first handle 114, the yaw rotation shaft 1121, the first actuation rotation shaft 1131a, and the second actuation rotation shaft 1131b connected to the pitch frame 1113 are rotated together. That is, if the pitch manipulation part 111 is rotated around the pitch rotation shafts 1111, the actuation manipulation part 113 and the yaw manipulation part 112 are rotated together with the pitch manipulation part 111. In other words, if a user rotates the first handle 114 around the pitch rotation shaft 1111, the actuation manipulation part 113, the yaw manipulation part 112, and the pitch manipulation part 111 are moved together.

The pitch manipulation part 111, the first jaw pitch pulley-a 111P1a, the first jaw pitch pulley-b 111P1b, the second jaw pitch pulley-a 111P2a, and the second jaw pitch pulley-b 111P2b are coupled to the pitch frame 1113. In this case, the first jaw pitch pulley-a 111P1a, the first jaw pitch pulley-b 111P1b, the second jaw pitch pulley-a 111P2a, and the second jaw pitch pulley-b 111P2b are coupled to the pitch rotation shaft 1111 in a manner rotatable around the pitch rotation shaft 1111.

Here, the first jaw pitch pulley-a 111P1a and the first jaw pitch pulley-b 111P1b may face each other and may be independently rotated. Therefore, an inward wire and an outward wire may be respectively wound around separate pulleys and thus may not interfere with each other. Similarly, the second jaw pitch pulley-a 111P2a and the second jaw pitch pulley-b 111P2b may face each other and may be independently rotated. Therefore, an inward wire and an outward wire may be respectively wound around separate pulleys and thus may not interfere with each other.

Referring to FIG. 7, the pitch wire end pulley 115P is fixedly coupled to the pitch frame 1113 and rotatable together with the pitch frame 1113. In addition, the pitch wire 130P is fixedly coupled to the pitch frame 1113 through a pitch wire auxiliary pulley 115S and the pitch wire end pulley 115P. As a result, the pitch frame 1113 and the pitch wire end pulley 115P may be rotated together around the pitch rotation shaft 1111 by pitch rotation.

The pitch wire 130P is operated as follows.

The pitch pulley 123P is fixedly coupled to the end tool hub 123a of the end tool 120, and the manipulation part 110 includes the pitch wire end pulley 115P, wherein the pitch pulley 123P and the pitch wire end pulley 115P are connected to each other through the pitch wire 130P such that pitch motion of the end tool 120 may be easily performed by pitch-manipulating the manipulation part 110. Here, both ends of the pitch wire 130P are fixedly coupled to the pitch frame 1113 respectively through the pitch wire auxiliary pulley 115S and the pitch wire end pulley 115P, and the pitch wire end pulley 115P is also fixedly coupled to the pitch frame 1113. That is, the pitch frame 1113 and the pitch wire end pulley 115P are rotated together about the pitch rotation shaft 1111 by pitch rotation of the manipulation part, and as a result, both sides of the pitch wire 130P are also moved in opposite directions such that additional power for pitch rotation may be transmitted independently of pitch motion of the end tool by the first jaw wire 130J1 and the second jaw wire 130J2.

The first handle 114, the pitch manipulation part 111, the yaw manipulation part 112, and the actuation manipulation part 113 are connected as follows. The actuation rotation shafts 1131a and 1131b, the yaw rotation shaft 1121, and the pitch rotation shaft 1111 may be provided on the first handle 114. In this case, since the actuation rotation shafts 1131a and 1131b are directly provided on the first handle 114, and the first handle 114 and the actuation manipulation part 113 may be directly connected to each other. In addition, since the yaw rotation shaft 1121 is directly provided on the first handle 114, the first handle 114 and the yaw manipulation part 112 may be directly connected to each other. However, since the pitch manipulation part 111 is provided at a side of the yaw manipulation part 112 and connected to the yaw manipulation part 112, the pitch manipulation part 111 may not be directly connected to the first handle 114 but may be indirectly connected to the first handle 114 through the yaw manipulation part 112.

Referring to the drawings, in the instrument 100 for surgery according to the first embodiment of the present disclosure, the pitch manipulation part 111 and the end tool 120 may be provided on the same axis or on parallel axes (to the X axis). That is, the pitch rotation shaft 1111 of the pitch manipulation part 111 is provided on an end portion of the bent part 141 of the connecting part 140, and the end tool 120 is provided on the other end portion of the connecting part 140.

In addition, one or more relay pulleys MP may be placed on a middle portion of the connecting part 140, particularly, on the bent part 141 of the connecting part 140 to change paths of wires or guide wires. At least portions of wires may be wound around the relay pulleys MP, thereby guiding paths of the wires and arranging the wires along a bent shape of the bent part 141.

In the drawings, it is illustrated that the connecting part 140 includes the bent part 141 and has a curved shape with a predetermined radius of curvature. However, the idea of the present disclosure is not limited thereto. If necessary, the connecting part 140 may have a straight shape or may be bent at least one time, and even in this case, it may be stated that the pitch manipulation part 111 and the end tool 120 are provided substantially on the same axis or parallel axes. In addition, although FIG. 3 illustrates that the pitch manipulation part 111 and the end tool 120 are provided on an axis parallel to the X axis, the idea of the present disclosure is not limited thereto. For example, the pitch manipulation part 111 and the end tool 120 may be provided on different axes.

Hereinafter, the ring handle 150 of the instrument 100 for surgery according to an embodiment of the present disclosure will be described in more detail.

Figure 9:
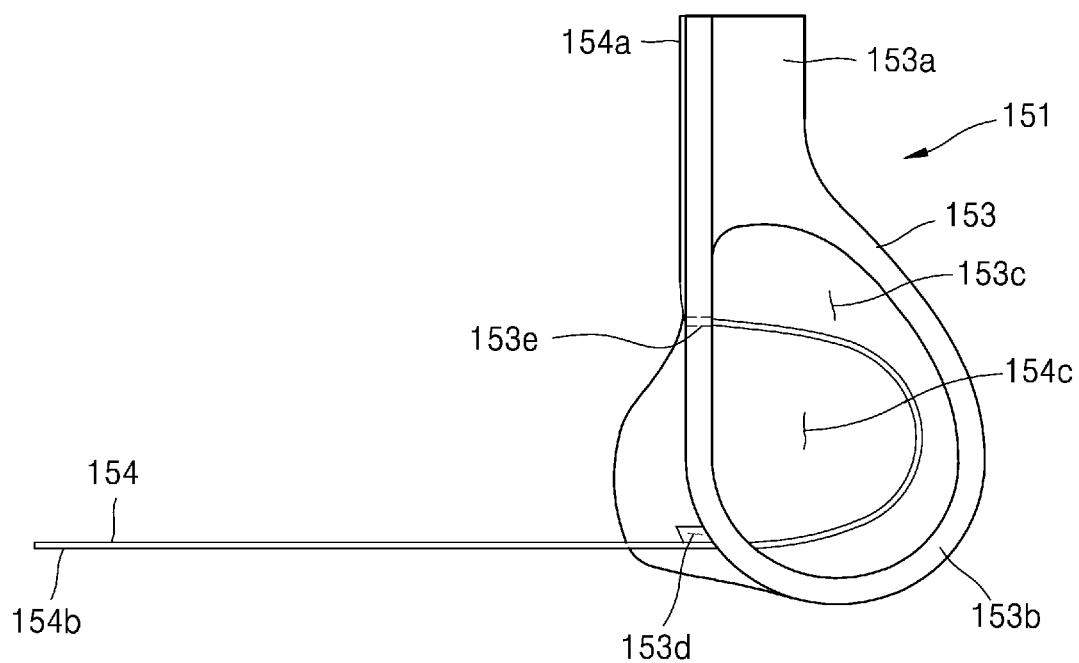
FIGS. 9, 10, and 11 are plan views illustrating a ring handle of the instrument for surgery of FIG. 2.
Figure 10:
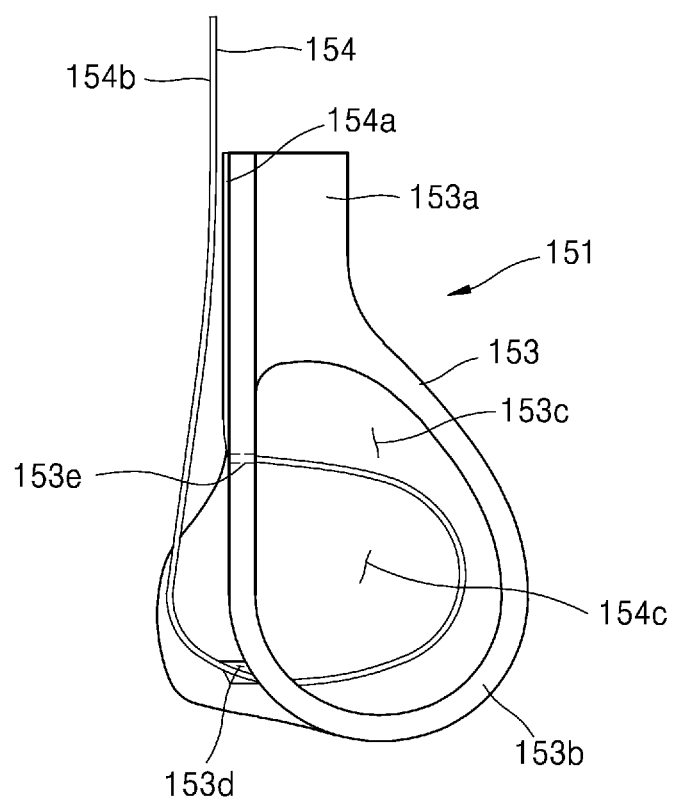
Figure 11:
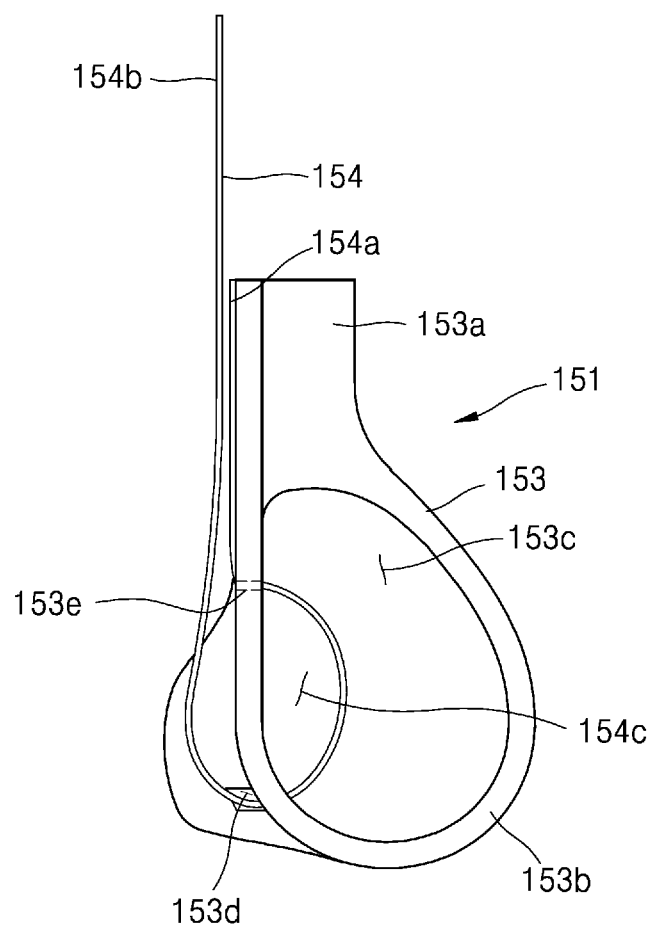

FIGS. 9, 10 and 11 are plan views illustrating the ring handle of the instrument for surgery of FIG. 2, FIG. 9 being a view illustrating a state in which a first end portion 154a and a second end portion 154b of the variable ring portion 154 are not fastened to each other, FIG. 10 being a view illustrating a state in which the first end portion 154a and the second end portion 154b of the variable ring portion 154 are fastened to each other to form a relatively large finger receiving hole 154c, and FIG. 11 being a view illustrating a state in which the finger receiving hole 154c of the variable ring portion 154 is formed smaller than in the state shown in FIG. 10.

According to the embodiment of the present disclosure, the ring handle 150 of the instrument 100 for surgery may include the first ring handle 151 and the second ring handle 152 as a pair. In addition, each of the ring handles 151 and 152 may include the fixed ring portion 153 and the variable ring portion 154. Hereinafter, the following description will be given based on the first ring handle 151 into which a user's thumb will be inserted, and the second ring handle 152 into which a user's index finger will be inserted may be symmetrical to the first ring handle 151 in a left-right direction.

Referring to FIGS. 9, 10, and 11, the first ring handle 151 may include the fixed ring portion 153 and the variable ring portion 154.

The fixed ring portion 153 has a hollow portion 153c formed therein such that a user's finger may be inserted in the hollow portion 153c. In detail, the fixed ring portion 153 includes a base 153a and a ring frame 153b which is connected to the base 153a and in which the hollow portion 153c is formed. In addition, one or more through-holes 153d and 153e may be formed in the ring frame 153b.

One end portion of the base 153a is coupled to the second actuation rotation part 1132b (FIG. 8) such that the first ring handle 151 may be rotated together with the second actuation rotation part 1132b (FIG. 8). In the drawings, the first ring handle 151 and the second actuation rotation part 1132b (FIG. 8) are illustrated as separate members. However, the idea of the present disclosure is not limited thereto, and it is also possible that the first ring handle 151 and the second actuation rotation part 1132b (FIG. 8) are formed in one piece.

The ring frame 153b is formed on the other end portion of the base 153a. The ring frame 153b has a ring shape as being termed such that the hollow portion 153c may be formed in the ring frame 153b.

The one or more through-holes 153d and 153e may be formed in the ring frame 153b. The through-holes 153d and 153e may be formed corresponding to the shape and thickness of the variable ring portion 154 such that the variable ring portion 154 may pass through the through-holes 153d and 153e. In the drawing, it is illustrated that two through-holes are formed. However, the idea of the present disclosure is not limited thereto, and the number of through-holes may be variously selected according to factors such as the shapes, lengths, and required features of the fixed ring portion 153 and the variable ring portion 154.

The variable ring portion 154 may be formed in a band shape having a predetermined width, and at least a portion of the variable ring portion 154 may be arranged within the fixed ring portion 153 and may be varied in shape within the fixed ring portion 153.

Here, it is possible to adjust the shape of the variable ring portion 154 according to the shape of a user's finger.

To this end, the variable ring portion 154 may be Velcro, particularly double-sided Velcro. That is, the variable ring portion 154 may be formed using Velcro, which is relatively easy to attach and detach, such that a user's finger may be fitted into or tightly coupled to the ring handle 150 by adjusting the attachment position of the Velcro in a state in which the user's finger is inserted in the ring handle 150.

Here, the first end portion 154a of the variable ring portion 154 may be fixedly coupled to the base 153a of the fixed ring portion 153. In addition, the second end portion 154b of the variable ring portion 154 may form the finger receiving hole 154c having an approximately circular shape while the second end portion 154b passes through the two through-holes 153e and 153d in sequence. After passing through the through-hole 153d, the second end portion 154b of the variable ring portion 154 may be attached to a predetermined region of the first end portion 154a of the variable ring portion 154, and thus the overall position and shape of the variable ring portion 154 may be approximately fixed.

In this case, depending on the position at which the second end portion 154b of the variable ring portion 154 is fastened to the first end portion 154a of the variable ring portion 154, the size and shape of the finger receiving hole 154c formed in the variable ring portion 154 may vary.

For example, in a state in which the first end portion 154a and the second end portion 154b of the variable ring portion 154 are not fastened to each other as shown in FIG. 9, the size of the finger receiving hole 154c may be freely varied by pushing or pulling the second end portion 154b.

In addition, referring FIG. 10, the first end portion 154a and the second end portion 154b of the variable ring portion 154 are fastened to each other, and the finger receiving hole 154c is formed to have a relatively large size.

In addition, referring to FIG. 11 both ends of the Velcro are attached to each other in a state in which the second end portion 154b is pulled furthermore, and thus the finger receiving hole 154c of the variable ring portion 154 is formed relatively smaller than in FIG. 10.

Here, as the variable ring portion 154, double-sided Velcro provided in a band shape having a predetermined width is illustrated, but the idea of the present disclosure is not limited thereto. Any variable ring portion having a structure for adjusting the size of a ring according to a user may be used. For example, a variable ring portion may be provided like a wrist watch in which a protrusion is formed on one side, and a plurality of holes into which the protrusion is insertable are formed in the other side, such that the size of the variable ring portion may be adjusted according to the hole into which the protrusion is inserted. In addition, a variable ring portion including a material having a predetermined degree of adhesiveness may be used such that the size of the variable ring portion may be adjusted while repeating attachment and detachment a plurality of times at an appropriate position. In addition, any other various attachment/detachment structures may be used.

As described above, the instrument 100 for surgery of the embodiment of the present disclosure includes the variable ring portion 154 of which the hole size is adjustable according to the thickness of a user's finger, such that the user's finger may be fitted into or tightly coupled to the ring handle 150, and convenience in manipulation may be improved.

Actuation, yaw, and pitch motions in the present embodiment are described below.

First, actuation motion is described below.

In a state in which a user inserts his/her index finger in the first actuation rotation part 1132a and the second ring handle 152 and his/her thumb in the second actuation rotation part 1132b and the first ring handle 151, if the user rotates the actuation rotation parts 1132a and 1132b using one or both of his/her index finger and thumb, the first actuation pulley 113P1 and the first actuation gear 1134a fixedly coupled to the first actuation rotation part 1132a are rotated around the first actuation rotation shaft 1131a, and the second actuation pulley 1133b and the second actuation gear 1134b fixedly coupled to the second actuation rotation part 1132b are rotated around the second actuation rotation shaft 1131b. At this time, the first actuation pulley 113P1 and the second actuation pulley 113P2 are rotated in opposite directions, and thus the first jaw wire 130J1 fixedly coupled to the first actuation pulley 113P1 at an end portion thereof and the second jaw wire 130J2 fixedly coupled to the second actuation pulley 113P2 at an end portion thereof are also moved in opposite directions. Then, rotating force is transmitted to the end tool 120 through the power transmission part 130, and two jaws 121 and 122 of the end tool 120 perform an actuation motion.

Here, as described above, the actuation motion refers to a motion in which the two jaws 121 and 122 are splayed or closed while being rotated in opposite directions. That is, if the actuation rotation parts 1132a and 1132b of the actuation manipulation part 113 are rotated toward each other, the first jaw 121 is rotated counterclockwise, and the second jaw 122 is rotated clockwise, thereby closing the end tool 120. If the actuation rotation parts 1132a and 1132b of the actuation manipulation part 113 are rotated away from each other, the first jaw 121 is rotated clockwise, and the second jaw 122 is rotated counterclockwise, thereby opening the end tool 120. In the present embodiment, the first and second actuation rotation parts 1132a and 1132b function as a second hand for actuation motion, and the second handle may be manipulated by gripping the second handle two fingers. However, the actuation manipulation part 113 for actuation motion in which two jaws of the end tool 120 are opened or closed may be configured in a manner different from the aforementioned manner. In a modification example, the first actuation pulley 113P1 and the second actuation pulley 113P2 may be oppositely driven using a single actuation rotation part.

Next, yaw motion will be described below.

If a user rotates the first handle 114 around the yaw rotation shaft 1121 while holding the first handle 114, the actuation manipulation part 113 and the yaw manipulation part 112 are rotated around the yaw rotation shaft 1121 in yaw motion. That is, if the first actuation pulley 113P1 of the first actuation manipulation part 113a to which the first jaw wire 130J1 is fixedly coupled is rotated around the yaw rotation shaft 1121, the first jaw wire 130J1 wound around the first jaw yaw pulley 112P1 is moved. Likewise, if the second actuation pulley 113P2 of the second actuation manipulation part 113b to which the second jaw wire 130J2 is fixedly coupled is rotated around the yaw rotation shaft 1121, the second jaw wire 130J2 wound around the second jaw yaw pulley 112P2 is moved. At this time, the first jaw wire 130J1 connected to the first jaw 121 and the second jaw wire 130J2 connected to the second jaw 122 are wound around the first jaw yaw pulley 112P1 and the second jaw yaw pulley 112P2 in such a manner that the first jaw 121 and the second jaw 122 are rotated in the same direction in the yaw motion. Then, rotating force is transmitted to the end tool 120 via the power transmission part 130, and thus the two jaws 121 and 122 of the end tool 120 are rotated in the same direction in yaw motion.

At this time, since the yaw frame 1123 connects the first handle 114, the yaw rotation shaft 1121, the first actuation rotation shaft 1131a, and the second actuation rotation shaft 1131b to each other, the first handle 114, the yaw manipulation part 112, and the actuation manipulation part 113 are rotated together around the yaw rotation shaft 1121.

Next, pitch motion will be described below.

If a user rotates the first handle 114 around the pitch rotation shaft 1111 while holding the first handle 114, the actuation manipulation part 113, the yaw manipulation part 112, and the pitch manipulation part 111 are rotated around the pitch rotation shaft 1111 in pitch motion. That is, if the first actuation pulley 113P1 of the first actuation manipulation part 113a to which the first jaw wire 130J1 is fixedly coupled is rotated around the pitch rotation shaft 1111, the first jaw wire 130J1 wound around the first jaw pitch pulley-a 111P1a and the first jaw pitch pulley-b 111P1b is moved. Likewise, if the second actuation pulley 113P2 of the second actuation manipulation part 113b to which the second jaw wire 130J2 is fixedly coupled is rotated around the pitch rotation shaft 1111, the second jaw wire 130J2 wound around the second jaw pitch pulley-a 111P2a and the second jaw pitch pulley-b 111P2b is moved. At this time, as described with reference to FIG. 5, while both strands of the first jaw wire 130J1 are rotated in the same direction, and both strands of the second jaw wire 130J2 are rotated in the same direction, the first jaw wire 130J1 and the second jaw wire 130J2 are wound around the first jaw pitch pulleys 111P1a and 111P1b and the second jaw pitch pulleys 111P2a and 111P2b such that the first jaw 121 and the second jaw 122 may be pitch-rotated. Then, rotating force is transmitted to the end tool 120 via the power transmission part 130, and thus the two jaws 121 and 122 of the end tool 120 perform a pitch motion.

At this time, since the pitch frame 1113 is connected to the yaw frame 1123 and the yaw frame 1123 connects the first handle 114, the yaw rotation shaft 1121, the first actuation rotation shaft 1131a, and the second actuation rotation shaft 1131b to each other, if the pitch frame 1113 is rotated around the pitch rotation shaft 1111, the yaw frame 1123, the first handle 114, the yaw rotation shaft 1121, the first actuation rotation shaft 1131a, and the second actuation rotation shaft 1131b connected to the pitch frame 1113 are rotated together. That is, if the pitch manipulation part 111 is rotated around the pitch rotation shaft 1111, the actuation manipulation part 113 and the yaw manipulation part 112 are rotated together with the pitch manipulation part 111.

In short, according to the instrument 100 for surgery of the embodiment of the present disclosure, pulleys are respectively provided on joint points (a actuation joint, a yaw joint, and a pitch joint), wires (the first jaw wire or the second jaw wire) are wound around the pulleys, such that if the manipulation part is rotated (actuation rotation, yaw rotation, or pitch rotation), each wire is moved for a desired motion of the end tool 120. Furthermore, an auxiliary pulley may be provided at a side of each pulley, and a wire may not be wound several times around the pulley owing to the auxiliary pulley.

Thus, as illustrated in FIG. 7 for describing the first embodiment, and actuation manipulation, yaw manipulation, and pitch manipulation may be independently performed.

As described with reference to FIG. 1, the actuation manipulation part 113, the yaw manipulation part 112, and the pitch manipulation part 111 are configured such that a rotation shaft is located behind each manipulation part like the joint configuration of the end tool, and thus a user may intuitively perform manipulations.

Particularly, in the instrument 100 for surgery of the embodiment of the present disclosure, a pulley provided on each joint point (an actuation joint, an yaw joint, and a pitch joint), a wire (the first jaw wire or the second jaw wire) is wound around the pulley, and if a manipulation part is rotated (actuation rotation, yaw rotation, or pitch rotation), the wire is moved to induce a desired motion of the end tool 120. Furthermore, an auxiliary pulley may be provided on a side of each pulley. Owing to the auxiliary pulley, a wire may not be wound several times around the pulley, wires wound around the pulley may not be in contact with each other, and a path for a wire running toward the pulley and wound around the pulley and a path in which a wire is wound around the pulley and leaves the pulley may be safely formed, thereby improving factors such as safety and efficient in power transmission.

In addition, as described above, the yaw manipulation part 112 and the actuation manipulation part 113 are directly provided on the first handle 114. Thus, if the first handle 114 is rotated about the pitch rotation shaft 1111, the yaw manipulation part 112 and the actuation manipulation part 113 are also rotated together with the first handle 114. Thus, the coordinate systems of the yaw manipulation part 112 and the actuation manipulation part 113 are not fixed, but relatively vary according to the rotation of the first handle 114. That is, drawings such as FIG. 2 illustrate that the yaw manipulation part 112 and the actuation manipulation part 113 are parallel with the Z axis. However, if the first handle 114 is rotated, the yaw manipulation part 112 and the actuation manipulation part 113 are not parallel with the Z axis. That is, the coordinate systems of the yaw manipulation part 112 and the actuation manipulation part 113 may change according to the rotation of the first handle 114. However, unless described otherwise, the coordinate systems of the yaw manipulation part 112 and the actuation manipulation part 113 are described based on the case in which the first handle 114 is perpendicular to the connecting part 140 as shown in FIG. 2 for ease of description.

Figure 12:
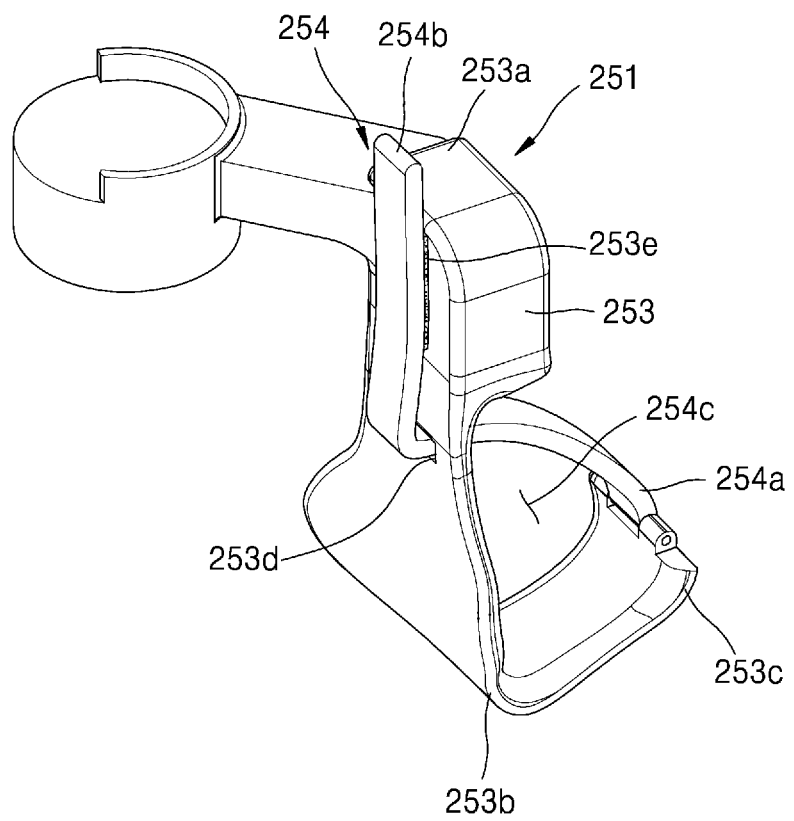
FIGS. 12 and 13 are perspective views illustrating an instrument for surgery according to another embodiment of the present disclosure.
Figure 13:
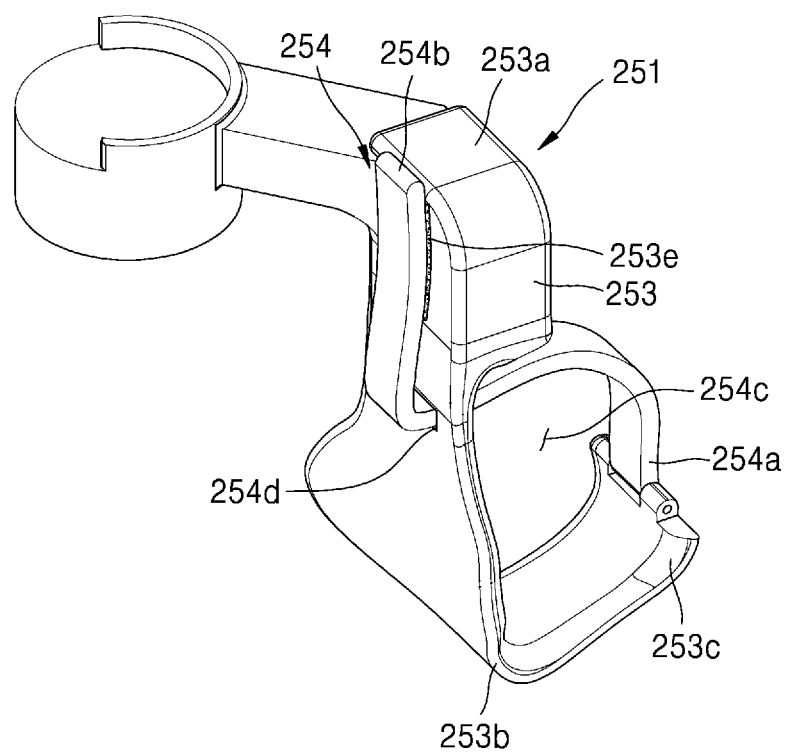

FIGS. 12 and 13 are perspective views illustrating an instrument for surgery according to another embodiment of the present disclosure.

Here, FIG. 12 is a view illustrating a state in which a state in which a second end portion 254b of a variable ring portion 254 is fastened to a fixed ring portion 253 to form a relatively small finger receiving hole 254c, and FIG. 13 is a view illustrating a state in which the finger receiving hole 254c of the variable ring portion 254 is formed larger than in the state shown in FIG. 12.

According to another embodiment of the present disclosure, a ring handle of the instrument for surgery may include a pair of a first ring handle 251 and a second ring handle (not shown). In addition, each of the first and second ring handles 251 may include the fixed ring portion 253 and the variable ring portion 254. Hereinafter, the following description will be given based on the first ring handle 251 into which a user's thumb will be inserted, and the second ring handle (not shown) into which a user's index finger will be inserted may be symmetrical to the first ring handle 251 in a left-right direction.

Referring to FIGS. 12 and 13, the first ring handle 251 may include the fixed ring portion 253 and the variable ring portion 254.

Here, in the embodiment of the present disclosure described with reference to FIG. 9, the fixed ring portion 153 (refer to FIG. 9) and the variable ring portion 154 (refer to FIG. 9) independently have ring shapes, but the present embodiment of the present disclosure is characteristically different therefrom in that the fixed ring portion 253 and the variable ring portion 254 of the first ring handle 251 of the instrument for surgery form a ring as being coupled to each other.

In detail, the fixed ring portion 253 includes a base 253a and a ring frame 253b which is coupled to the base 253a. In this case, the ring frame 253b has an open side unlike the closed loop type shown in FIG. 9, and thus the ring frame 253b includes an end portion 253c. In addition, at least one through-hole 253d may be formed in the ring frame 253b. In addition, a fastening portion 253e may be formed on a side of the base 253a off the fixed ring portion 253 such that the variable ring portion 254 may be fastened to the fastening portion 253e.

One end portion of the base 153a is coupled to the second actuation rotation part 1132b (FIG. 8) such that the first ring handle 251 may be rotated together with the second actuation rotation part 1132b (FIG. 8). In the drawings, the first ring handle 251 and the second actuation rotation part 1132b (FIG. 8) are illustrated as separate members. However, the idea of the present disclosure is not limited thereto, and it is also possible that the first ring handle 251 and the second actuation rotation part 1132b (FIG. 8) are formed in one piece.

The ring frame 253b is formed on the other end portion of the base 253a. As described above the ring frame 253b has an open side unlike the closed loop type shown in FIG. 9, and thus the ring frame 253b includes an end portion 253c.

The at least one through-hole 253d may be formed in the ring frame 253b. The through-hole 253d may be formed corresponding to the shape and thickness of the variable ring portion 254 such that the variable ring portion 254 may be inserted through the through-hole 253d. In the drawing, it is illustrated that one through-hole is formed. However, the idea of the present disclosure is not limited thereto, and the number of through-holes may be variously selected according to factors such as the shapes, lengths, and required features of the fixed ring portion 253 and the variable ring portion 254.

The variable ring portion 254 may be formed in a band shape having a predetermined width. Here, it is possible to adjust the shape of the variable ring portion 254 according to the shape of a user's finger.

To this end, the variable ring portion 254 may be Velcro, particularly double-sided Velcro. That is, the variable ring portion 254 may be formed using Velcro, which is relatively easy to attach and detach, such that a user's finger may be fitted into or tightly coupled to the ring handle 250 by adjusting the attachment position of the Velcro in a state in which the user's finger is inserted in the ring handle 250.

Here, a first end portion 254a of the variable ring portion 254 may be fixedly coupled to the end portion 253c of the fixed ring portion 253. In this case, the first end portion 254a of the variable ring portion 254 and the end portion 253c of the fixed ring portion 253 may be coupled to each other by a coupling method such as a hinge coupling method for rotation relative to each other. As the first end portion 254a of the variable ring portion 254 and the end portion 253c of the fixed ring portion 253 are coupled to each other as described above, the formation of a ring is completed.

In addition, the second end portion 254b of the variable ring portion 254 may form the finger receiving hole 254c having an approximately circular shape while the second end portion 254b passes through the through-hole 253d. After passing through the through-hole 253d, the second end portion 254b of the variable ring portion 254 may be attached to a fastening portion 253e formed in a predetermined region of the base 253a of the fixed ring portion 253, and thus the overall position and shape of the variable ring portion 154 may be approximately fixed.

In this case, depending on a portion of the second end portion 254b of the variable ring portion 154 which is fastened to the fastening portion 253e of the fixed ring portion 253, the size and shape of the finger receiving hole 254c formed in the variable ring portion 254 may vary.

For example, in FIG. 12, the second end portion 254b of the variable ring portion 254 is attached to the fastening portion 253e in a state in which the second end portion 254b of the variable ring portion 254 is pulled to some degree such that the finger receiving hole 254c may be formed to have a relatively small size.

In contrast, referring to FIG. 13, the second end portion 254b is attached to the fastening portion 253e in a state in which the second end portion 254b is pulled to a relatively less extent such that the finger receiving hole 254c of the variable ring portion 254 may be formed larger than in FIG. 12.

Here, as the variable ring portion 254, Velcro provided in a band shape having a predetermined width is illustrated, but the idea of the present disclosure is not limited thereto. Any variable ring portion having a structure for adjusting the size of a ring according to a user may be used. For example, a variable ring portion may be provided like a wrist watch in which a protrusion is formed on one side, and a plurality of holes into which the protrusion is insertable are formed in the other side, such that the size of the variable ring portion may be adjusted according to the hole into which the protrusion is inserted. In addition, a variable ring portion including a material having a predetermined degree of adhesiveness may be used such that the size of the variable ring portion may be adjusted while repeating attachment and detachment a plurality of times at an appropriate position. In addition, any other various attachment/detachment structures may be used.

As described above, the instrument for surgery of the embodiment of the present disclosure includes the variable ring portion 254 of which the hole size is adjustable according to the thickness of a user's finger, such that the user's finger may be fitted into or tightly coupled to the ring handle 250, and convenience in manipulation may be improved.

Figure 14:
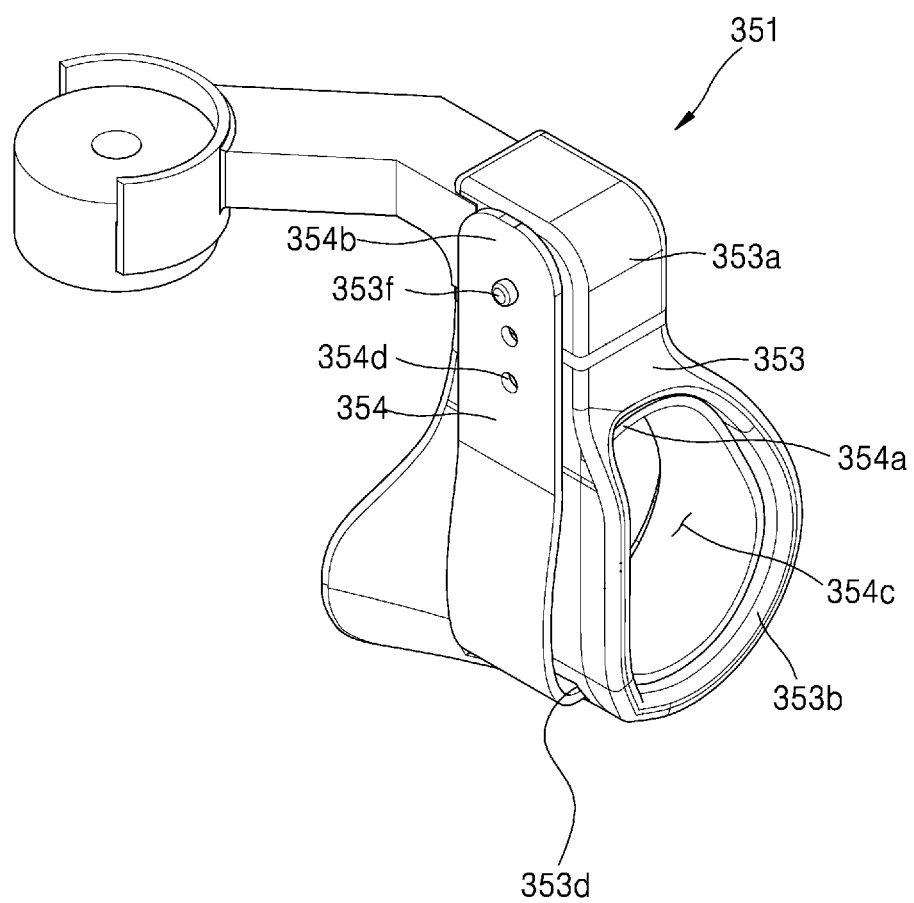
FIGS. 14 and 15 are perspective views illustrating an instrument for surgery according to another embodiment of the present disclosure.
Figure 15:
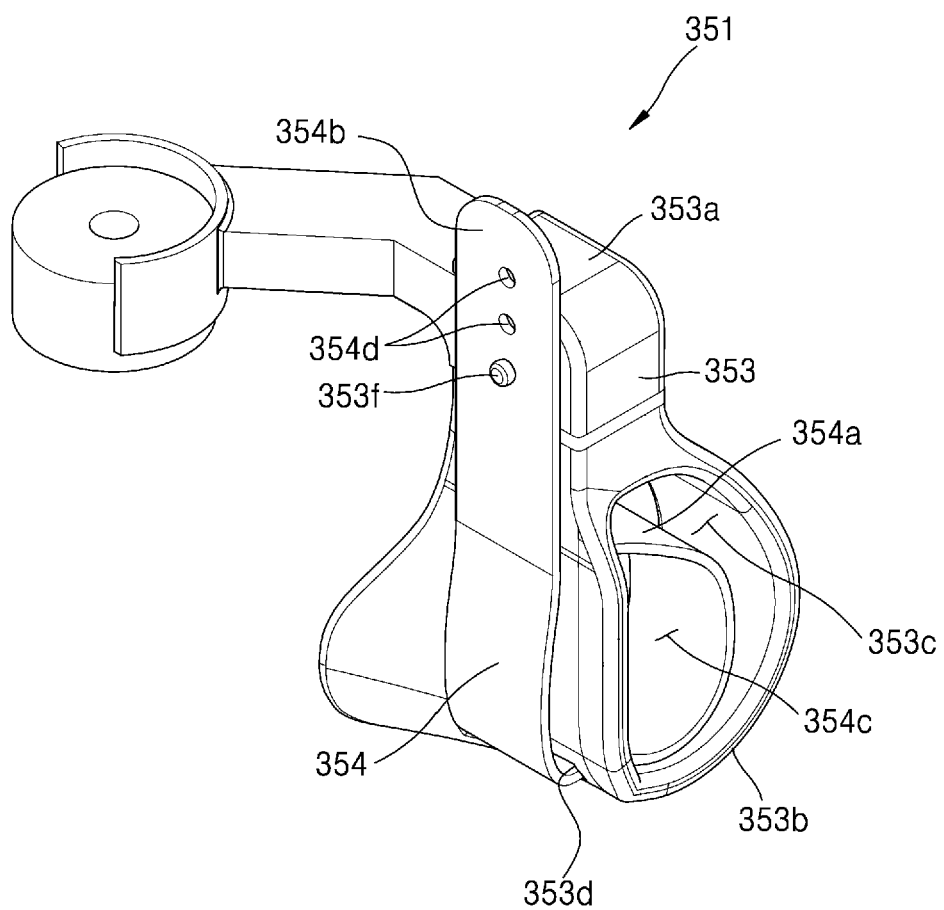

FIGS. 14 and 15 are perspective views illustrating an instrument for surgery according to another embodiment of the present disclosure.

FIGS. 14 and 15 are perspective views illustrating a ring handle of the instrument for surgery according to another embodiment of the present disclosure, FIG. 10 being a view illustrating a state in which a protrusion 353f of a fixed ring portion 353 is inserted into a hole 354d of a variable ring portion 354 to form a relatively large finger receiving hole 354c, and FIG. 15 being a view illustrating a state in which the finger receiving hole 354c of the variable ring portion 354 is formed to have a relatively small size.

According to another embodiment of the present disclosure, the ring handle of the instrument for surgery may include a pair of a first ring handle 351 and a second ring handle (not shown). In addition, each of the first and second ring handles 351 may include the fixed ring portion 353 and the variable ring portion 354. Hereinafter, the following description will be given based on the first ring handle 351 into which a user's thumb will be inserted, and the second ring handle (not shown) into which a user's index finger will be inserted may be symmetrical to the first ring handle 351 in a left-right direction.

Here, in the embodiment of the present disclosure described with reference to FIG. 9 or the like, the variable ring portion 154 (refer to FIG. 9) is formed of Velcro, but the present embodiment of the present disclosure is characteristically different therefrom in that the fixed ring portion 353 and the variable ring portion 354 of the first ring handle 351 are coupled to each other by a protrusion-hole coupling method.

The fixed ring portion 353 has a hollow portion 353c formed therein such that a user's finger may be inserted in the hollow portion 353c. In detail, the fixed ring portion 353 includes a base 353a and a ring frame 353b which is connected to the base 353a and in which the hollow portion 353c is formed. In addition, at least one through-hole 353d may be formed in the ring frame 353b.

One end portion of the base 353a is coupled to the second actuation rotation part 1132b (FIG. 8) such that the first ring handle 351 may be rotated together with the second actuation rotation part 1132b (FIG. 8). In the drawings, the first ring handle 351 and the second actuation rotation part 1132b (FIG. 8) are illustrated as separate members. However, the idea of the present disclosure is not limited thereto, and it is also possible that the first ring handle 351 and the second actuation rotation part 1132b (FIG. 8) are formed in one piece.

The ring frame 353b is formed on the other end portion of the base 353a. The ring frame 353b has a ring shape as being termed such that the hollow portion 353c may be formed in the ring frame 353b.

The at least one through-hole 353d may be formed in the ring frame 353b. The through-hole 353d may be formed corresponding to the shape and thickness of the variable ring portion 354 such that the variable ring portion 354 may be inserted through the through-hole 353d. In the drawing, it is illustrated that one through-hole is formed. However, the idea of the present disclosure is not limited thereto, and the number of through-holes may be variously selected according to factors such as the shapes, lengths, and required features of the fixed ring portion 353 and the variable ring portion 354.

In addition, the protrusion 353f may be formed on a side of the base 353a of the fixed ring portion 353 for coupling with the variable ring portion 354.

The variable ring portion 354 may be formed in a band shape having a predetermined width, and at least a portion of the variable ring portion 354 may be arranged within the fixed ring portion 353 and may be varied in shape within the fixed ring portion 353.

Here, it is possible to adjust the shape of the variable ring portion 354 according to the shape of a user's finger.

To this end, one or more holes 354d may be formed in the variable ring portion 354. In addition, the protrusion 353f of the fixed ring portion 353 is insertable into any one of the holes 354d such that a user's finger may be fitted into or tightly coupled to the first ring handle 351 by inserting the protrusion 353f into a proper one of the holes 354d in a state in which the user's finger is inserted into the first ring handle 351.

Here, a first end portion 354a of the variable ring portion 354 may be fixedly coupled to one of the base 353a and the ring frame 353b of the fixed ring portion 353. In the drawings, the first end portion 354a of the variable ring portion 354 is coupled to an inner side of the ring frame 353b. However, the idea of the present disclosure is not limited thereto. For example, as in the embodiment described with reference to FIG. 9, the first end portion 354a of the variable ring portion 354 may be fixed to the base 353a of the fixed ring portion 353 and may then be inserted into the ring frame 353b through a through-hole.

In addition, a second end portion 354b of the variable ring portion 354 may form the finger receiving hole 354c having an approximately circular shape while the second end portion 354b passes through the through-hole 353d. After inserting the second end portion 354b of the variable ring portion 354 through the through-hole 353d, the second end portion 354b of the variable ring portion 354 may be attached to the protrusion 353f formed in a predetermined region of the base 353a of the fixed ring portion 353, and thus the overall position and shape of the variable ring portion 354 may be approximately fixed.

At this time, the size and shape of the finger receiving hole 354c formed by coupling the fixed ring portion 353 and the variable ring portion 354 to each other may be determined depending on which of the holes 354d of the variable ring portion 354 is coupled to the protrusion 353f of the fixed ring portion 353.

For example, in FIG. 14, the protrusion 353f of the fixed ring portion 353 is inserted into the second end portion 354b of the variable ring portion 354, and the finger receiving hole 354c is formed to have a relatively large size.

However, in FIG. 15, the protrusion 353f of the fixed ring portion 353 is inserted into the second end portion 354b of the variable ring portion 354 in a state in which the second end portion 354b of the variable ring portion 354 is further pulled, and thus the finger receiving hole 354c of the variable ring portion 354 is formed larger than in FIG. 14.

Here, it is illustrated that the protrusion 353f is formed on the fixed ring portion 353, and one or more holes 354d are formed in the variable ring portion 354. However, the idea of the present disclosure is not limited thereto, and if necessary, other structures such as a structure in which the holes 354d and the protrusion 353f are formed to the contrary may be applied.

As described above, the instrument for surgery of the embodiment of the present disclosure includes the variable ring portion 354 of which the hole size is adjustable according to the thickness of a user's finger, such that the user's finger may be fitted into or tightly coupled to a ring handle 350, and convenience in manipulation may be improved.

While embodiments of the present disclosure have been described with reference to the accompanying drawings, these embodiments are for illustrative purposes only, and it will be understood by those of ordinary skill in the art that various changes and modifications may be made therein. Therefore, the scope and spirit of the present disclosure should be defined by the following claims.

INDUSTRIAL APPLICABILITY

The present disclosure relates to an instrument for surgery and, more specifically, to an instrument for surgery which may be manually operated and used for laparoscopic surgery or various other types of surgery.

The invention claimed is:

1. An instrument for surgery comprising:
an end tool comprising a first jaw and a second jaw that are rotatable, the end tool being rotatable in at least two directions;
a manipulation part configured to control rotation of the end tool in the at least two directions;

a power transmission part connected to the manipulation part, the power transmission part comprising a first jaw wire that transmits rotation of the manipulation part to the first jaw and a second jaw wire that transmits rotation of the manipulation part to the second jaw; and a connecting part extending in a first direction (X axis), the connecting part being coupled to the end tool at an end portion thereof and coupled to the manipulation part at another end portion thereof so as to connect the manipulation part to the end tool, wherein the manipulation part is formed to be extended toward the end tool, and a formation direction of the end tool on the one end portion of the connecting part and a formation direction of the manipulation on the other end portion of the connecting part are the same based on the axis (X axis) along which the connecting part extends, wherein the manipulation part comprises:

an actuation manipulation part configured to control actuation motion of the end tool; and a ring handle formed on an end portion of the actuation manipulation part, the ring handle comprising a fixed ring portion and a variable ring portion to receive a user's finger therein, wherein the fixed ring portion comprises:

a base;

a ring frame which is connected to the base and in which the hollow portion is formed; and at least one through-hole formed in the ring frame, wherein at least a portion of the fixed ring portion is arranged within the fixed ring portion and is variable in shape within the fixed ring portion, a first end portion of the variable ring portion is fixedly coupled to the base, and a second end portion of the variable ring portion forms a finger receiving hole while passing through the at least one through-hole.

2. The instrument for surgery of claim 1, wherein an attachment position of the variable ring portion is adjustable according to a shape of the user's finger.

3. The instrument for surgery of claim 1, wherein the variable ring portion is varied in shape according to a position at which the second end portion of the variable ring portion is fastened to the first end portion of the variable ring portion.

4. The instrument for surgery of claim 1, wherein the actuation manipulation part comprises two actuation manipulation parts, and the ring handle comprises two ring handles.

5. The instrument for surgery of claim 4, wherein when the two ring handles are rotated together in approaching directions, the two jaws of the end tool are rotated together in approaching directions.

6. The instrument for surgery of claim 1, wherein the variable ring portion comprises Velcro.

7. The instrument for surgery of claim 1, wherein the variable ring portion comprises a protrusion or a hole, and a hole or a protrusion having a shape corresponding to the protrusion or the hole of the variable ring portion is formed on one of the fixed ring portion and the variable ring portion.

8. The instrument for surgery of claim 1, wherein the manipulation part further comprises:

a first handle;

a yaw manipulation part connected to the first handle and configured to control yaw motion of the end tool; and a pitch manipulation part formed at a side of the yaw manipulation part and configured to control pitch motion of the end tool, wherein the actuation manipulation part is formed on another side of the yaw manipulation part.

9. An instrument for surgery comprising:

an end tool comprising a first jaw and a second jaw that are rotatable, the end tool being rotatable in at least two directions;

a manipulation part configured to control rotation of the end tool in the at least two directions;

a power transmission part connected to the manipulation part, the power transmission part comprising a first jaw wire that transmits rotation of the manipulation part to the first jaw and a second jaw wire that transmits rotation of the manipulation part to the second jaw; and a connecting part extending in a first direction (X axis), the connecting part being coupled to the end tool at an end portion thereof and coupled to the manipulation part at another end portion thereof so as to connect the manipulation part to the end tool, wherein the manipulation part is formed to be extended toward the end tool, and a formation direction of the end tool on the one end portion of the connecting part and a formation direction of the manipulation on the other end portion of the connecting part are the same based on the axis (X axis) along which the connecting part extends, wherein the manipulation part comprises:

an actuation manipulation part configured to control actuation motion of the end tool; and a ring handle formed on an end portion of the actuation manipulation part, the ring handle comprising a fixed ring portion and a variable ring portion to receive a user's finger therein, wherein the fixed ring portion comprises:

a base;

a ring frame which is connected to the base and in which the hollow portion is formed; and at least one through-hole formed in the ring frame, wherein at least a portion of the fixed ring portion is arranged within the fixed ring portion and is variable in shape within the fixed ring portion, a first end portion of the variable ring portion is fixedly coupled to the ring frame, and a second end portion of the variable ring portion forms a finger receiving hole while passing through the at least one through-hole.

10. The instrument for surgery of claim 9, wherein an attachment position of the variable ring portion is adjustable according to a shape of the user's finger.

11. The instrument for surgery of claim 9, wherein the variable ring portion is varied in shape according to a position at which the second end portion of the variable ring portion is coupled to a protrusion formed on the fixed ring portion.

12. The instrument for surgery of claim 9, wherein the variable ring portion comprises Velcro.

13. The instrument for surgery of claim 9, wherein the manipulation part further comprises:

a first handle;

a yaw manipulation part connected to the first handle and configured to control yaw motion of the end tool; and a pitch manipulation part formed at a side of the yaw manipulation part and configured to control pitch motion of the end tool, wherein the actuation manipulation part is formed on another side of the yaw manipulation part.

14. An instrument for surgery comprising:
an end tool comprising a first jaw and a second jaw that are rotatable, the end tool being rotatable in at least two directions;
a manipulation part configured to control rotation of the end tool in the at least two directions;
a power transmission part connected to the manipulation part, the power transmission part comprising a first jaw wire that transmits rotation of the manipulation part to the first jaw and a second jaw wire that transmits rotation of the manipulation part to the second jaw; and
a connecting part extending in a first direction (X axis), the connecting part being coupled to the end tool at an end portion thereof and coupled to the manipulation part at another end portion thereof so as to connect the manipulation part to the end tool,
wherein the manipulation part is formed to be extended toward the end tool, and
a formation direction of the end tool on the one end portion of the connecting part and a formation direction of the manipulation on the other end portion of the connecting part are the same based on the axis (X axis) along which the connecting part extends,
wherein the manipulation part comprises:
an actuation manipulation part configured to control actuation motion of the end tool; and
a ring handle formed on an end portion of the actuation manipulation part, the ring handle comprising a fixed ring portion and a variable ring portion to receive a user's finger therein,
wherein a side of the fixed ring portion is open to form an end portion, and
a first end portion of the variable ring portion is coupled to the end portion of the fixed ring portion, and a second end portion of the variable ring portion is coupled to a region of the fixed ring portion other than the end portion of the fixed ring portion to form a finger receiving hole into which the user's finger is insertable.

15. The instrument for surgery of claim 14, wherein an attachment position of the variable ring portion is adjustable according to a shape of the user's finger.

16. The instrument for surgery of claim 14, wherein the fixed ring portion comprises:
a base;
a ring frame which is connected to the base and is open at a side thereof to form the end portion; and
at least one through-hole formed in the ring frame.

17. The instrument for surgery of claim 16, wherein the first end portion of the variable ring portion is coupled to the end portion of the fixed ring portion, and
the second end portion of the variable ring portion forms the finger receiving hole while passing through the at least one through-hole.

18. The instrument for surgery of claim 17, wherein the variable ring portion is varied in shape according to a position at which the second end portion of the variable ring portion is fastened to a fastening portion of the fixed ring portion.

19. The instrument for surgery of claim 14, wherein the variable ring portion comprises Velcro.

20. The instrument for surgery of claim 14, wherein the manipulation part further comprises:
a first handle;
a yaw manipulation part connected to the first handle and configured to control yaw motion of the end tool; and
a pitch manipulation part formed at a side of the yaw manipulation part and configured to control pitch motion of the end tool,
wherein the actuation manipulation part is formed on another side of the yaw manipulation part.

* * * * *